United States Patent
Han et al.

(10) Patent No.: US 7,202,024 B2
(45) Date of Patent: Apr. 10, 2007

(54) BBC3 GENE PROMOTER AND METHODS FOR IDENTIFYING MODULATORS OF APOPTOSIS AND BBC3 GENE EXPRESSION USING A BBC3 GENE PROMOTER

(75) Inventors: Jia-Wen Han, Newton, MA (US); Thomas Chittenden, Stow, MA (US)

(73) Assignee: Immunogen Inc., Cambridge, MA (US)

( * ) Notice: Subject to any disclaimer, the term of this patent is extended or adjusted under 35 U.S.C. 154(b) by 727 days.

(21) Appl. No.: 09/953,133

(22) Filed: Sep. 17, 2001

(65) Prior Publication Data

US 2003/0059776 A1     Mar. 27, 2003

(51) Int. Cl.
*C12Q 1/68* (2006.01)

(52) U.S. Cl. .................... 435/6; 536/23.1; 536/24.1; 435/7.1; 436/501; 436/518

(58) Field of Classification Search ................ 536/23.1
See application file for complete search history.

(56) References Cited

FOREIGN PATENT DOCUMENTS

| WO | WO 99/50280 A1 | 10/1999 |
|----|----------------|---------|
| WO | WO 00/60092 A2 | 10/2000 |
| WO | WO 01/23522 A2 | 4/2001 |
| WO | WO 02064790 A2 | 8/2002 |

OTHER PUBLICATIONS

NCBI accession No. AC000852.5 (Jul. 18, 2000) downloaded from NCBI website on May 5, 2005.*
Nakano, et al., *PUMA, a Novel Proapoptotic Gene, is Induced by p53*, Mol. Cell 7:684-694 (2001).
Yu, et al., *PUMA Induces the Rapid Apoptosis of Colorectal Cancer Cell*, Mol. Cell 7:673-682 (2001).
Han et al. *PNAS USA* 98(20):11318-11323(2001).

* cited by examiner

*Primary Examiner*—Misook Yu
(74) *Attorney, Agent, or Firm*—Sughrue Mion, PLLC

(57) ABSTRACT

The present invention is directed to methods for identifying compounds that modulate apoptosis, directly or indirectly, as measured by changes in expression of the bbc3 gene or a reporter gene, or by changes in the apoptotic character of a cell. The present invention is also directed to methods for identifying compounds that modulate expression of the bbc3 gene and a method for identifying compounds that interact with a promoter of the bbc3 gene. The present invention is further directed to a method for modulating apoptosis in a cell, a method for modulating bbc3 gene expression in a cell, a process for making a modulator of apoptosis, and a process for making a modulator of bbc3 gene expression. Finally, the present invention is directed to compounds identified by each of the methods of this invention, and to promoters of the bbc3 gene and sequences homologous thereto.

83 Claims, 9 Drawing Sheets

A

```
hBbc3  MARARQEGSSPEPVEGLARDGPRPFPLGRLVPSAVSCGLCEPGLAAAPAA   50
mBbc3  MARARQEGSSPEPVEGLARDSPRPFPLGRLMPSAVSCSLCEPGLPAAPAA   50 hBbc3  PTLLPAAYLCAPTAPPAVTAALGGSRWPGGPRSRPRGPRPDGPQPSLSLA  100
mBbc3  PALLPAAYLCAPTAPPAVTAALGGPRWPGGHRSRPRGPRPDGPQPSLSPA  100

BH3
hBbc3  EQHLESPVPSAPGALAGGPTQAAPGVRGEEEQWAREIGAQLRRMADDLNA  150
mBbc3  QQHLESPVPSAPEALAGGPTQAAPGVRVEEEEWAREIGAQLRRMADDLNA  150 hBbc3  QYERRRQEEQQRHRPSPWRVLYNLIMGLLPLPRGHRAPEMEPN  193
mBbc3  QYERRRQEEQHRHRPSPWRVMYNLFMGLLPLPRDPGAPEMEPN  193
```

B

```
                            BH3
Bbc3   133   WAREIGAQLRRMADDLNAQY
Egl-1   50   IGYEIGSKLAAMCDDFDAQM
Bad    106   AAQRYGRELRRMSDEFVDSF
Bim     84   PEIWIAQELRRIGDEFNAYY
Bid     82   IIRNIARHLAQVGDSMDRSI
Bik     53   GSDALALRLACIGDEMDVSL
Hrk     29   AAQLTAARLKALGDELHQRT
```

Fig. 1

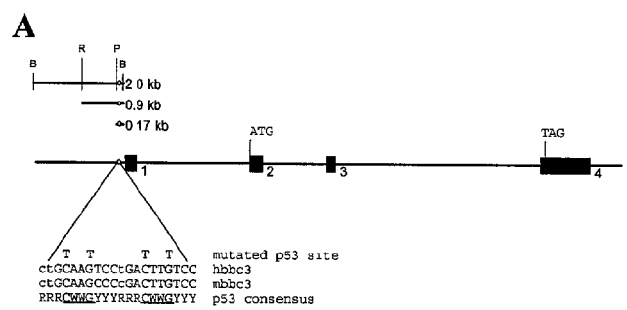
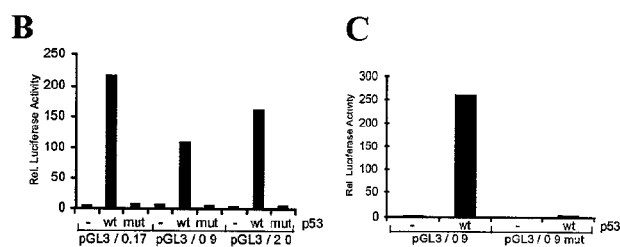
Fig. 4

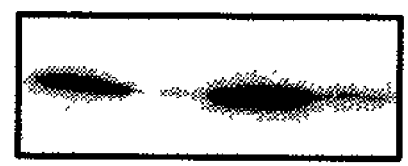
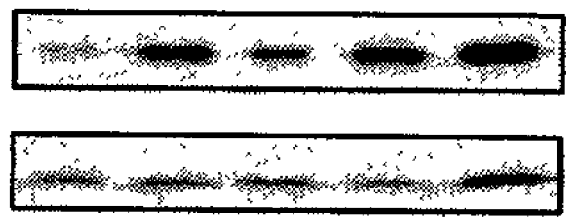
Fig. 7

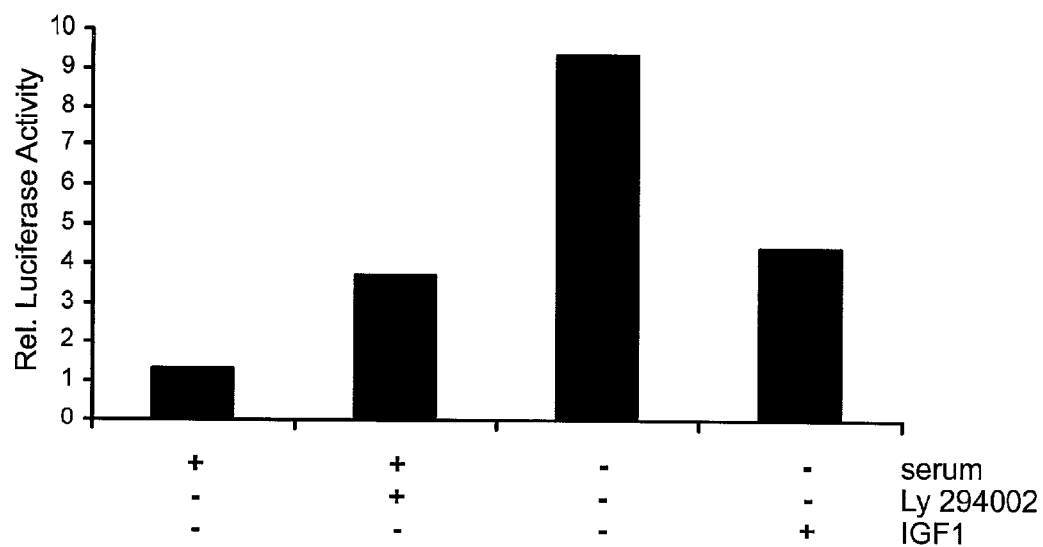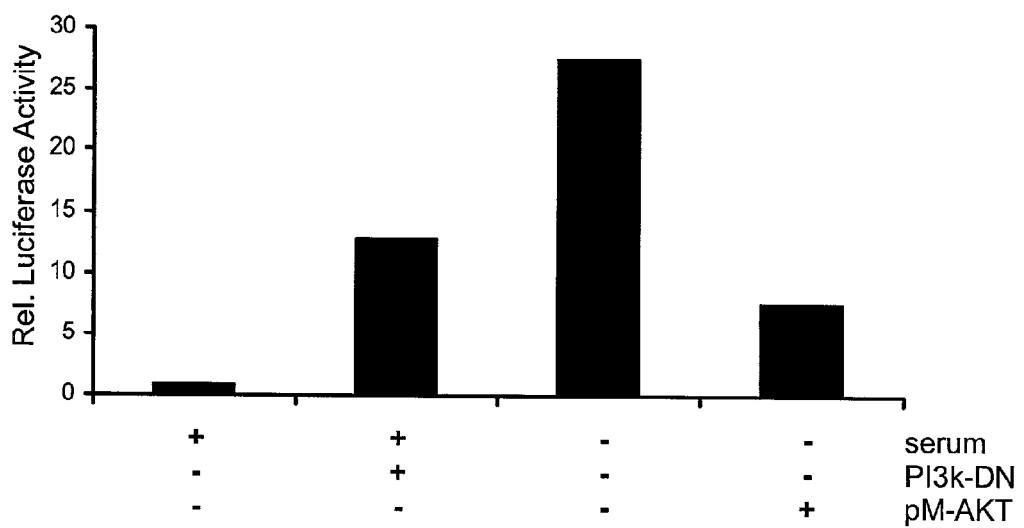
Fig. 8

```
GGATCCCGAG GTCAGGAGTT TGAGACCAGC CTGGCCAATA TGGTGAAACC GCATCTCTAC   60
BamHI
CAATAATACA AAAATTAGCT GGGCATAGTG GCGCACACCT GTAGTCCCAG CTACTAGGGA  120
GGCTGAGGCA GAAGACTTGC TTGAACCCAG GAGGCGGAGG TGGCAATGAG CCGAGATCAT  180
GCCACTGAAC TCCAGCCTGG GCGACAGCGC GAGACTCTGT CTCAAAAAAA AAAAAAAAG   240
TAAGATCCAT GTAAGTGATG TCATATGTCA TAATCCATGG TTTACTCATG ACCCACAGTT  300
TGGAAAACAC CAGGAAGAAG GAAGGGACAA TGAATAATCG GGGAAAGCGA AAGAGGAGGG  360
AAAGTGAAAG AGGGAGGAAA GCTGAGGAGT TCCCAATGTT GCAAATGGGG AGATTTCACG  420
TGAGATATAG ATTACCTGCA TCTCTTGGGG GAGCTAAGAG TGTGTACTTG GAGGCAGTCA  480
AGTTTGAGAA GTCTGACATC CTTACTCAGC CAGCCCCACA CTAGGCACTG GAAGGTGAGT  540
CACTCTGGTG AGGCGATTGC GATTGGGTGA GACCCAGTAA GGATGGAAAG TGTAGAGGAG  600
ACAGGAATCC ACGGCTTTGG AAAAGGAAG GACAAAACTC ACCAAACCAG AGCAGGGCAG  660
GAAGTAACAA TGAGAAACTG AAAAAGAAAC GGAATGGAAA GCTATGAGAC AGGATGAAAT  720
TTGGCATGGG GTCTGCCCAG GCATGTCCAT GCCAGGTGCC CAGGGCTGCT TCCACGACGT  780
GGGTCCCCTG CCAGATTTGT GGTGAGTGTG GCCAGGTGTG CATGCTCCGA CGTGTGTGCA  840
GTGGGCCAGT TAGCAAGAAG CTGTCACAGG TGTGACTTTG TGACATGTGT GGGTGGTCAG  900
TTTCTTCTAT GTCTGATTTG GTTTGTGTCT CTGAATGTCA GTTTCTTTCC TTTATTTTA   960
TTTTTAAGAC GGAGTTTGCT CTTGTTGCCC AGGCTAGAGT GCAATGGCAC TATCTCGGCT 1020
CACTGCAACC TCCGCCTCCC GGGTTCAAGC AGTTCTCCTG CCTCAGCCTC CAAGTAGCT  1080
GGGATTACAG GCATGCGCCA CAACGCCCGG CTAATTTTGT ATTTTTAGTA GAGATGGGGT 1140
TTCATCATGT TGGTCAGGCT GGTCTCGAAT TCCTGACCTC AGGCAGTCCA CGCACCTTGG 1200
                              EcoRI
CCTCCCAAAG TGCTGGGATT ACAGGCATGA GCCACCGTGT CGGGCGAATG TCACTTTCTG 1260
ATAGTTTTAA TGTGTTAGCT GTGAAATTGT GTGAGTGCAT TTGTGTATGT CCCTGTGGGA 1320
GTGTGATTTG GATTTGGCCG TGTATCCAGG TATCCCTGTA ACAGGTGTCT GTGTGTATGT 1380
GTGTGTCCCC TGTGCCTATC AGCAAGTTTG TGTTTCCTGA TAAGCACTCC GCCTATGTCT 1440
GTGTGGTTGC ACCACCGTGT GTGTGGTGTG GGTGCCTGTT CGGTAGGGTT GTTTGTGAAC 1500
ACAGTTTGTG GGCCCAGGTG TGATCATCAG TGTGGGTGTT TCTGCAACTG TGTGTGGCCC 1560
TGTCATTGTG TCCGTCTGCT TGTCCAGGGG ACCCTGTTAG TGAGTCTGTG CATTTCCGTC 1620
TGGGTGTGTG TAAGTGTGAG CCCCATCAGT ATGTGAGTGT GTGTGCTCAT GCCCTGTCC  1680
ATGGTGTGGA TTTGCGAGAC TGTGGCCTTG TGTCTGTGAG TACATCCTCT GGGCTCTGCC 1740
TGCACGTGAC TTTGTGGACC CTGGAACGCC CGTCGGTCGG TCTGTGTACG CATCGCTGGG 1800
GGTGTGGATC TGTGGGTCCC AGTCAGTGTG TGTGTCCGAC TGTCCCGGTG TCTGGGCGAT 1860
CTCCCCACAC CCCGCCGCAC AGCGCCTGGG TCCTCCTTGC CTTGGGCTAG GCCCTGCCCC 1920
GTCCCCCGCT GCAGGGAAAC CCCCGGCGCG GAGGTAGGGG GGGCGCGGC GCGCGCCTGC 1980
        PstI
AAGTCCTGAC TTGTCCGCGG CGGGCGGGCG GGGCCGTAGC GTCACGCGGG GGCGGGGCGT 2040
GGGACCCGCC GGGCGGGGGC GGGGCGGGGC GGGGCGGGGC GGCTTTGGAG CGGGCCCGGG 2100
ATCC                                                              2104
BamHI
```

BBC3 GENE PROMOTER AND METHODS FOR IDENTIFYING MODULATORS OF APOPTOSIS AND BBC3 GENE EXPRESSION USING A BBC3 GENE PROMOTER

BACKGROUND OF THE INVENTION

1. Field of the Invention

The present invention is directed to methods for identifying compounds that modulate apoptosis, directly or indirectly, as measured by changes in expression of the bbc3 gene or a reporter gene, or by changes in the apoptotic character of a cell.

The present invention is also directed to methods for identifying compounds that modulate expression of the bbc3 gene and a method for identifying compounds that interact with a promoter of the bbc3 gene.

The present invention is further directed to a method for modulating apoptosis in a cell, a method for modulating bbc3 gene expression in a cell, a process for making a modulator of apoptosis, and a process for making a modulator of bbc3 gene expression.

Finally, the present invention is directed to compounds identified by each of the methods of this invention, and to promoters of the bbc3 gene and sequences homologous thereto.

2. Description of the Related Art

Bcl-2 family proteins regulate the cellular response to apoptotic stimuli (Adams, J. M., et al., *Science* 281:1322–6 (1998); Korsmeyer, S. J., *Cancer Res.* 59:1693s–1700s (1999)). Members of this family can function to either suppress or promote cell death, and are characterized by the presence of up to four different conserved amino acid motifs, termed Bcl-2 homology (BH) domains (Adams, J. et al., *Science* 281:1322–6 (1998); Korsmeyer, S. J., *Cancer Res.* 59:1693s–1700s (1999)). The BH3 domain is a uniquely important functional element within the pro-apoptotic class of Bcl-2 related proteins, mediating the ability of these proteins to dimerize with other Bcl-2 related proteins, and promote apoptosis (Chittenden, T., et al., *Nature* 374:733–6 (1995); Huang, D. C., et al., *Cell* 103:839–42 (2000)). The function of BH3 as a cell death domain has been further revealed by an emerging group of 'BH3-only' proteins, which share only BH3 in common with other Bcl-2 family members. This class of proteins, which includes Bik, Bad, Bid, Bim, Egl-1 and Hrk, induce apoptosis by binding, through the BH3 domain, to anti-apoptotic members of the Bcl-2 family (Huang, D. C., et al., *Cell* 103:839–42 (2000)).

Biochemical and genetic evidence indicates that BH3-only proteins function at a point upstream of Bcl-2 in a cell death pathway conserved in both vertebrates and invertebrates (Huang, D. C., et al., *Cell* 103:839–42 (2000); Horvitz, H. R., *Cancer Res.* 59:1701s–1706s (1999)). BH3-only proteins have been shown to localize to mitochondria following apoptotic stimuli, where they bind to Bcl-2 family members and induce mitochondrial events associated with apoptosis, including the release of cytochrome c into the cytosol (Huang, D. C., et al., *Cell* 103:839–42 (2000)). The functions of the BH3 proteins Bad and Bid are regulated by phosphorylation and proteolytic activation, respectively, in response to extrinsic cell survival/cell death stimuli (Zha, J., et al., *Cell* 87:619–28 (1996); Luo, X., et al., *Cell* 94:481–90 (1998); Li, H., et al., *Cell* 94:491–501 (1998)). Through post-translational modifications, Bad and Bid transduce signals originating at cell surface receptors to a Bcl-2-regulated, mitochondrial apoptosis control point.

In *C. elegans*, the BH3-only protein Egl-1 operates at the most proximal point in a genetically-defined pathway required for all programmed cell death (Conradt, B., et al., *Cell* 93:519–29 (1998)). Egl-1 binds to the nematode Bcl-2 counterpart, Ced-9, and antagonizes its function, similar to the function ascribed to mammalian BH3 proteins. By contrast to Bad and Bid, the activity of Egl-1 appears to be regulated primarily through transcriptional control mechanisms. The egl-1 gene is active specifically in cells that are destined to die during development, and genetic studies have identified transcription factors upstream of egl-1 that control its expression in certain cell lineages (Conradt, B., et al., *Cell* 98:317–27 (1999); Metzstein, M. M., et al., *Nature* 382:545–7 (1996); Metzstein, M. M., et al., *Mol. Cell.* 4:309–19 (1999)).

There is a remarkable degree of structural and functional conservation between the genes that control the cell death pathway in nematodes and mammals (Horvitz, H. R., *Cancer Res.* 59:1701s–1706s (1999)). The essential contribution of Egl-1 and its transcriptional regulation to programmed cell death in *C. elegans* strongly implies that apoptosis in mammalian cells may depend on the transcriptional control of gene(s) encoding BH3-only proteins. Disregulation of the mechanisms that control transcription of BH3-only genes in this class may contribute to defects in apoptosis in diseases such as cancer.

The present inventors recently identified a strongly pro-apoptotic BH3-only protein, termed Bbc3 (Bcl-2 binding component 3), encoded by a gene (bbc3) (the human bbc3 cDNA, promoter and protein sequences can be found at GenBank accession numbers U82987, AF411827 and AAB51243, respectively) that is subject to transcriptional regulation by multiple cell death signaling pathways. Experimental results have indicated that transcriptional control of the bbc3 gene contributes to cell death regulation in mammalian cells. Bbc3 gene expression is activated by at least three apoptotic stimuli, including DNA damage, glucocorticoid treatment, and growth factor deprivation, constituting a broad transcriptional response thus far unique among mammalian cell death regulatory genes. By analogy to egl-1, the bbc3 gene may prove to be induced in other contexts as well, for example, during developmental cell deaths. Thus, expression of the bbc3 gene may serve to transduce cell death signals originating from diverse stimuli to common mitochondrial apoptotic events regulated by the Bcl-2 family.

Due to the apparent broad role of Bbc3 in pathways leading to apoptosis, the identification of compounds that modulate the effects of Bbc3 could lead to the development of therapeutic agents. Indeed, the identification of compounds that modulate bbc3 gene expression, and those that modulate activity of the Bbc3 protein, could potentially be used in the treatment of medical conditions such as cancers where the normal apoptotic pathways have been blocked (e.g. leukemia), and neuronal degenerative diseases, such as Parkinson's disease, where apoptosis is accelerated.

In addition, the bbc3 gene could be used to identify components of the bbc3 signal transduction pathway, as well as components of other pathways involved in apoptosis. Compounds that modulate these pathways could also be important therapeutic agents useful for treating a range of medical conditions.

Accordingly, methods of identifying compounds that modulate both apoptosis and the activity of the bbc3 gene could serve to identify potential therapeutic compounds, as well as identify other targets for treatment of medical conditions where apoptosis is involved. The present invention is directed to these and other important objectives.

SUMMARY OF THE INVENTION

Thus, the objectives of the present invention include providing methods for identifying a compound that modulates apoptosis, methods for identifying a compound that modulates bbc3 gene expression, a method for identifying a compound that interacts with a bbc3 gene promoter, a method for modulating apoptosis, a method for modulating bbc3 gene expression, a method for making a compound that modulates apoptosis, a method for making a compound that modulates bbc3 gene expression, providing compounds identified by these methods, and bbc3 gene promoters and sequences homologous thereto.

These and other objectives have been achieved by providing, isolating and characterizing at least a portion of the human bbc3 gene promoter (SEQ ID NO: 1).

The present invention provides methods for identifying compounds that modulate apoptosis.

In one embodiment, the present invention provides a method for identifying a compound that modulates apoptosis, the method comprising (a) providing a cell containing a polynucleotide encoding a bbc3 gene promoter operably linked to either a bbc3 gene or a reporter gene, (b) exposing the cell to a candidate compound, and (c) determining expression of the bbc3 gene or the reporter gene, wherein a change in expression is an indication that the candidate compound modulates apoptosis.

Preferably, the determining is performed by detecting expression of bbc3 mRNA, reporter gene mRNA, Bbc3 protein or reporter gene protein, or the determining is performed by assaying the capacity of Bbc3 for inducing death of the cell.

Preferably, the reporter gene is selected from the group consisting of a polynucleotide encoding a luciferase enzyme, an alkaline phosphatase enzyme, a β-galactosidase enzyme and a chloramphenicol acetyltransferase enzyme.

Preferably, the bbc3 gene promoter comprises a polynucleotide selected from the group consisting of nucleotides 1934–2099 of the sequence set forth in SEQ ID NO: 1, nucleotides 1168–2099 of the sequence set forth in SEQ ID NO: 1, nucleotides 1–2099 of the sequence set forth in SEQ ID NO: 1, and polynucleotides homologous thereto.

Preferably, the method further comprises exposing the cell to one or more inducers and/or inhibitors of apoptosis at any time before exposing the cell to the candidate compound, at any time after exposing the cell to the candidate compound or simultaneous with exposure of the cell to the candidate compound.

Preferably, the one or more inducers and/or inhibitors is selected from the group consisting of a growth factor, absence of a growth factor, an agent of DNA damage, a glucocorticoid, p53 and a kinase inhibitor.

In a preferred embodiment, the present invention provides a method for identifying a compound that modulates apoptosis, the method comprising (a) providing a cell containing a polynucleotide encoding a bbc3 gene promoter operably linked to either a bbc3 gene or a reporter gene, (b) culturing the cell in the presence of serum, (c) culturing the cell in the absence of serum, (d) exposing the cell to a candidate compound, and (e) determining expression of the bbc3 gene or the reporter gene, wherein a change in expression is an indication that the candidate compound modulates apoptosis.

Preferably, the expression of the bbc3 gene or the reporter gene is down-regulated by the candidate compound.

Preferably, the determining is performed by detecting expression of bbc3 mRNA, reporter gene mRNA, Bbc3 protein or reporter gene protein, or by assaying the capacity of Bbc3 for inducing death of the cell.

Preferably, the reporter gene is selected from the group consisting of a polynucleotide encoding a luciferase enzyme, an alkaline phosphatase enzyme, a β-galactosidase enzyme and a chloramphenicol acetyltransferase enzyme.

Preferably, the bbc3 gene promoter comprises a polynucleotide selected from the group consisting of nucleotides 1934–2099 of the sequence set forth in SEQ ID NO: 1, nucleotides 1168–2099 of the sequence set forth in SEQ ID NO: 1, nucleotides 1–2099 of the sequence set forth in SEQ ID NO: 1, and polynucleotides homologous thereto.

Preferably, the method further comprises exposing the cell to one or more inducers and/or inhibitors of apoptosis at any time before exposing the cell to the candidate compound, at any time after exposing the cell to the candidate compound or simultaneous with exposure of the cell to the candidate compound.

Preferably, the one or more inducers and/or inhibitors is selected from the group consisting of a growth factor, absence of a growth factor, an agent of DNA damage, a glucocorticoid, p53 and a kinase inhibitor.

In another preferred embodiment, the present invention provides a method for identifying a compound that modulates apoptosis, the method comprising (a) providing a cell containing a polynucleotide encoding a bbc3 gene promoter operably linked to either a bbc3 gene or a reporter gene, (b) culturing the cell in the presence of serum, (c) culturing the cell in the absence of serum, (d) exposing the cell to a compound known to inhibit bbc3 gene promoter activity, (e) exposing the cell to a candidate compound, and (f) determining expression of the bbc3 gene or the reporter gene, wherein a change in expression is an indication that the candidate compound modulates apoptosis.

Preferably, the expression of the bbc3 gene or the reporter gene is up-regulated by the candidate compound.

Preferably, the determining is performed by detecting expression of bbc3 mRNA, reporter gene mRNA, Bbc3 protein or reporter gene protein, or by assaying the capacity of Bbc3 for inducing death of the cell.

Preferably, the reporter gene is selected from the group consisting of a polynucleotide encoding a luciferase enzyme, an alkaline phosphatase enzyme, a β-galactosidase enzyme and a chloramphenicol acetyltransferase enzyme.

Preferably, the bbc3 gene promoter comprises a polynucleotide selected from the group consisting of nucleotides 1934–2099 of the sequence set forth in SEQ ID NO: 1, nucleotides 1168–2099 of the sequence set forth in SEQ ID NO: 1, nucleotides 1–2099 of the sequence set forth in SEQ ID NO: 1, and polynucleotides homologous thereto.

Preferably, the method further comprises exposing the cell to one or more inducers and/or inhibitors of apoptosis at any time before exposing the cell to the candidate compound, at any time after exposing the cell to the candidate compound or simultaneous with exposure of the cell to the candidate compound.

Preferably, the one or more inducers and/or inhibitors is selected from the group consisting of a growth factor, absence of a growth factor, an agent of DNA damage, a glucocorticoid, p53 and a kinase inhibitor.

The present invention also provides methods for identifying compounds that modulate bbc3 gene expression in a cell.

In one embodiment, the present invention provides a method for identifying a compound that modulates bbc3 gene expression, the method comprising (a) providing a cell containing a polynucleotide encoding a bbc3 gene promoter operably linked to either a bbc3 gene or a reporter gene, (b) exposing the cell to a candidate compound, and (c) determining expression of the bbc3 gene or the reporter gene, wherein a change in expression is an indication that the candidate compound modulates bbc3 gene expression.

Preferably, the determining is performed by detecting expression of bbc3 mRNA, reporter gene mRNA, Bbc3 protein or reporter gene protein, or by assaying the capacity of Bbc3 for inducing death of the cell.

Preferably, the reporter gene is selected from the group consisting of a polynucleotide encoding a luciferase enzyme, an alkaline phosphatase enzyme, a β-galactosidase enzyme and a chloramphenicol acetyltransferase enzyme.

Preferably, the bbc3 gene promoter comprises a polynucleotide selected from the group consisting of nucleotides 1934–2099 of the sequence set forth in SEQ ID NO: 1, nucleotides 1168–2099 of the sequence set forth in SEQ ID NO: 1, nucleotides 1–2099 of the sequence set forth in SEQ ID NO: 1, and polynucleotides homologous thereto.

Preferably, the method further comprises exposing the cell to one or more inducers and/or inhibitors of bbc3 gene expression at any time before exposing the cell to the candidate compound, at any time after exposing the cell to the candidate compound or simultaneous with exposure of the cell to the candidate compound.

Preferably, the one or more inducers and/or inhibitors is selected from the group consisting of a growth factor, absence of a growth factor, an agent of DNA damage, a glucocorticoid, p53 and a kinase inhibitor.

In a preferred embodiment, the present invention provides a method for identifying a compound that modulates bbc3 gene expression, the method comprising (a) providing a cell containing a polynucleotide encoding a bbc3 gene promoter operably linked to either a bbc3 gene or a reporter gene, (b) culturing the cell in the presence of serum, (c) culturing the cell in the absence of serum, (d) exposing the cell to a candidate compound, and (e) determining expression of the bbc3 gene or the reporter gene, wherein a change in expression is an indication that the candidate compound modulates bbc3 gene expression.

Preferably, the expression of the bbc3 gene or the reporter gene is down-regulated by the candidate compound.

Preferably, the determining is performed by detecting expression of bbc3 mRNA, reporter gene mRNA, Bbc3 protein or reporter gene protein, or by assaying the capacity of Bbc3 for inducing death of the cell.

Preferably, the reporter gene is selected from the group consisting of a polynucleotide encoding a luciferase enzyme, an alkaline phosphatase enzyme, a β-galactosidase enzyme and a chloramphenicol acetyltransferase enzyme.

Preferably, the bbc3 gene promoter comprises a polynucleotide selected from the group consisting of nucleotides 1934–2099 of the sequence set forth in SEQ ID NO: 1, nucleotides 1168–2099 of the sequence set forth in SEQ ID NO: 1, nucleotides 1–2099 of the sequence set forth in SEQ ID NO: 1, and polynucleotides homologous thereto.

Preferably, the method further comprises exposing the cell to one or more inducers and/or inhibitors of bbc3 gene expression at any time before exposing the cell to the candidate compound, at any time after exposing the cell to the candidate compound or simultaneous with exposure of the cell to the candidate compound.

Preferably, the one or more inducers and/or inhibitors is selected from the group consisting of a growth factor, absence of a growth factor, an agent of DNA damage, a glucocorticoid, p53 and a kinase inhibitor.

In another preferred embodiment, the present invention provides a method for identifying a compound that modulates bbc3 gene expression, the method comprising (a) providing a cell containing a polynucleotide encoding a bbc3 gene promoter operably linked to either a bbc3 gene or a reporter gene, (b) culturing the cell in the presence of serum, (c) culturing the cell in the absence of serum, (d) exposing the cell to a compound known to inhibit bbc3 gene promoter activity, (e) exposing the cell to a candidate compound, and (f) determining expression of the bbc3 gene or the reporter gene, wherein a change in expression is an indication that the candidate compound modulates bbc3 gene expression.

Preferably, the expression of the bbc3 gene or the reporter gene is up-regulated by the candidate compound.

Preferably, the determining is performed by detecting expression of bbc3 mRNA, reporter gene mRNA, Bbc3 protein or reporter gene protein, or by assaying the capacity of Bbc3 for inducing death of the cell.

Preferably, the reporter gene is selected from the group consisting of a polynucleotide encoding a luciferase enzyme, an alkaline phosphatase enzyme, a β-galactosidase enzyme and a chloramphenicol acetyltransferase enzyme.

Preferably, the bbc3 gene promoter comprises a polynucleotide selected from the group consisting of nucleotides 1934–2099 of the sequence set forth in SEQ ID NO: 1, nucleotides 1168–2099 of the sequence set forth in SEQ ID NO: 1, nucleotides 1–2099 of the sequence set forth in SEQ ID NO: 1, and polynucleotides homologous thereto.

Preferably, the method further comprises exposing the cell to one or more inducers and/or inhibitors of bbc3 gene expression at any time before exposing the cell to the candidate compound, at any time after exposing the cell to the candidate compound or simultaneous with exposure of the cell to the candidate compound.

Preferably, the one or more inducers and/or inhibitors is selected from the group consisting of a growth factor, absence of a growth factor, an agent of DNA damage, a glucocorticoid, p53 and a kinase inhibitor.

The present invention also provides a cell-free or in vitro method for identifying compounds that modulate bbc3 gene expression.

Thus, the present invention provides a method for identifying a compound that modulates bbc3 gene expression, the method comprising (a) providing a composition comprising a polynucleotide encoding a bbc3 gene promoter operably linked to either a bbc3 gene or a reporter gene, (b) exposing the composition to a candidate compound, and (c) determining expression of the bbc3 gene or the reporter gene, wherein a change in expression is an indication that the candidate compound modulates bbc3 gene expression.

Preferably, the determining is performed by detecting expression of bbc3 mRNA, reporter gene mRNA, Bbc3 protein or reporter gene protein.

Preferably, the reporter gene is selected from the group consisting of a polynucleotide encoding a luciferase enzyme, an alkaline phosphatase enzyme, a β-galactosidase enzyme and a chloramphenicol acetyltransferase enzyme.

Preferably, the bbc3 gene promoter comprises a polynucleotide selected from the group consisting of nucleotides 1934–2099 of the sequence set forth in SEQ ID NO: 1, nucleotides 1168–2099 of the sequence set forth in SEQ ID NO: 1, nucleotides 1–2099 of the sequence set forth in SEQ ID NO: 1, and polynucleotides homologous thereto.

Preferably, the method further comprises exposing the composition to one or more inducers and/or inhibitors of bbc3 gene expression at any time before exposing the composition to the candidate compound, at any time after exposing the composition to the candidate compound or simultaneous with exposure of the composition to the candidate compound.

Preferably, the one or more inducers and/or inhibitors is selected from the group consisting of a growth factor, absence of a growth factor, an agent of DNA damage, a glucocorticoid, p53 and a kinase inhibitor.

The present invention also provides a method for identifying compounds that interact with the bbc3 gene promoter.

Thus, the present invention provides a method for identifying a compound that interacts with a bbc3 gene promoter, the method comprising (a) providing a bbc3 gene promoter, (b) contacting the promoter with a candidate compound, and (c) detecting an interaction between the promoter and the candidate compound, thereby identifying a compound that interacts with the bbc3 gene promoter.

Preferably, the bbc3 gene promoter comprises a polynucleotide selected from the group consisting of nucleotides 1934–2099 of the sequence set forth in SEQ ID NO: 1, nucleotides 1168–2099 of the sequence set forth in SEQ ID NO: 1, nucleotides 1–2099 of the sequence set forth in SEQ ID NO: 1, and polynucleotides homologous thereto.

Preferably, the detecting is performed using an antibody that recognizes and binds the candidate compound, performed using polymerase chain reaction or performed by gel retardation analysis.

Preferably, the bbc3 gene promoter is in a cell and the cell is contacted with the candidate compound.

The present invention also provides a method for modulating apoptosis.

Thus, the present invention includes a method for modulating apoptosis in a cell, the method comprising (a) providing a cell containing the bbc3 gene operably linked to a bbc3 gene promoter, and (b) contacting the cell with a compound identified in one of the above methods for modulating apoptosis, thereby modulating apoptosis in a cell.

Preferably, the modulating inhibits or induces apoptosis in a cell.

The present invention also provides a method for modulating bbc3 gene expression.

Thus, the present invention provides a method for modulating bbc3 gene expression, the method comprising (a) providing a cell containing the bbc3 gene operably linked to a bbc3 gene promoter, and (b) contacting the cell with a compound identified in one of the above methods for modulating bbc3 gene expression, thereby modulating bbc3 gene expression.

Preferably, the modulating inhibits or induces bbc3 gene expression.

The present invention also provides a method for making a compound that modulates apoptosis.

Thus, the present invention provides a method for making a modulator of apoptosis, the method comprising (a) carrying out any of the methods described herein for identifying a modulator of apoptosis, thereby identifying a compound that is a modulator of apoptosis, and (b) manufacturing the compound.

The present invention also provides a method for making a compound that modulates bbc3 gene expression.

Thus, the present invention provides a method for making a modulator of bbc3 gene expression, the method comprising (a) carrying out any of the methods described herein for identifying a modulator of bbc3 gene expression, thereby identifying a compound that is a modulator of bbc3 gene expression, and (b) manufacturing the compound.

In a further embodiment, the present invention provides a compound identified by any of the methods described herein.

In an additional embodiment, the present invention provides an isolated nucleic acid molecule comprising the polynucleotide sequence of bases 1–2099 of SEQ ID NO: 1, an isolated nucleic acid molecule comprising the polynucleotide sequence of bases 1168–2099 of SEQ ID NO: 1, and an isolated nucleic acid molecule comprising the polynucleotide sequence of bases 1934–2099 of SEQ ID NO: 1.

In a final embodiment, the present invention provides an isolated nucleic acid molecule comprising a polynucleotide sequence homologous to the polynucleotide sequence of bases 1–2099 of SEQ ID NO: 1, an isolated nucleic acid molecule comprising a polynucleotide sequence homologous to the polynucleotide sequence of bases 1168–2099 of SEQ ID NO: 1, and an isolated nucleic acid molecule comprising a polynucleotide sequence homologous to the polynucleotide sequence of bases 1934–2099 of SEQ ID NO: 1.

BRIEF DESCRIPTION OF THE DRAWINGS

FIG. 1A shows an alignment of human (hBbc3) (SEQ ID NO:2) and mouse (mBbc3) (SEQ ID NO:3) Bbc3 amino acid sequences with the BH3 domain (shaded), the KM140 antibody binding site (line), and non-identical residues (asterisks).

FIG. 1B shows an alignment of the BH3 domains of Bbc3 and other BH3-only family members. (Bbc3—SEQ ID NO:4; Egl-1—SEQ ID NO:5; Bad—SEQ ID NO:6; Bim—SEQ ID NO:7; Bid—SEQ ID NO:8; Bik—SEQ ID NO:9; Hrk—SEQ ID NO:10; Additional sequences shared by Bbc3 and Egl-1 are underlined; asterisks indicate Bbc3 residues mutated to alanine in the BH3-ala mutant.

FIG. 3A shows the induction of bbc3 mRNA in NIH3T3 cells upon treatment with etoposide (50 μM) for 6 hours.

FIG. 3B shows the induction of bbc3 mRNA in a E1a/Ras/p53MER mouse fibroblast cell line upon treatment with 4-hydroxy-tamoxifen (4-OHT, 100 nM) for 5 hours. FIG. 3C shows the induction of bbc3 mRNA upon the induction of wild-type p53 function in M1p53ts cells through shifting the temperature to 32° C. for 6 hours, also in the presence of IL-6.

FIG. 4A shows a schematic of the bbc3 gene structure, and cloned segments of the bbc3 gene promoter region. Restriction sites for BamHI, PstI and EcoRI are indicated by B, P, and R, respectively. The putative p53 binding sites in the human (hbbc3) (SEQ ID NO:11) and mouse (mbbc3) (SEQ ID NO:12) bbc3 gene promoter regions are shown, together with the consensus p53 binding site (SEQ ID NO:13) and substitution mutations introduced into the human site.

FIG. 4B shows the results of the transactivation of bbc3 gene promoters by wild-type p53. The bbc3 gene promoter region fragments shown in FIG. 4A were cloned into a luciferase reporter plasmid and co-transfected with plasmids expressing either wild-type p53 (wt) or mutant p53 (mut) into Saos-2 cells. Luciferase activity (measured in triplicate) was normalized to an internal transfection efficiency control (β-galactosidase).

FIG. 4C shows experimental evidence that mutation of the p53 binding site abolishes transactivation of the bbc3 gene promoter by p53. Transfections were performed as in FIG. 4B, with bbc3 gene promoter reporter plasmids containing an intact (pGL3/0.9) or mutated (pGL3/0.9mut) p53 binding site, in the presence or absence of wild-type p53.

FIG. 7A shows that the addition of the EGF receptor kinase inhibitor, AG1478, blocked the ability of EGF to suppress Bbc3 protein expression. HT29 cells were incubated for one day in the absence of serum (−), and then incubated in media containing either serum, 50 ng/ml EGF, or 50 ng/ml EGF+30 nM AG1478, for 24 hrs. Bbc3 was detected by western blot analysis.

FIG. 7B shows that the addition of the EGF receptor inhibitor, AG1478, blocked the ability of serum to suppress Bbc3 protein expression. HT29 cells were cultured in the presence of serum for one day (+) and then incubated for 24 hrs with serum or without serum, or in the presence of serum supplemented with either 10 μM PD98059, 30 μM AG1478, or 50 μM AG1024. Bbc3 was detected by western blot analysis, followed by reprobing of the blot with anti-Bax.

FIG. 8A shows the results of the activation of a bbc3 gene promoter by a PI-3 kinase inhibitor and suppression of bbc3 gene promoter activity by IGF-1. The pGL3/0.9 bbc3 gene promoter luciferase reporter plasmid was transfected into HeLa-Bcl-xL cells. At 24 hrs after transfection, cells were incubated for an additional 24 hrs in the presence of 20% serum (+) with or without 50 μM LY294002, or in the absence of serum (−) with or without 100 ng/ml IGF-1. Luciferase activity was measured and normalized for transfection efficiency (β-galactosidase).

FIG. 8B shows the regulation of bbc3 gene promoter activity by the PI-3 kinase/Akt pathway. The pGL3/0.9 bbc3 gene promoter luciferase reporter plasmid was co-transfected into HeLa-Bcl-xL cells either with a plasmid encoding a PI-3 Kinase-dominant negative mutant (PI3k-DN) or a pcDNA3 plasmid encoding a myristoylated AKT (pM-AKT). At 24 hrs after transfection, cells were incubated for an additional 24 hrs in the presence of 20% serum (+) or absence of serum (−). Luciferase activity was measured and normalized for transfection efficiency.

FIG. 9 shows the genomic DNA sequence of 2.0 kb of the human bbc3 gene promoter (SEQ ID NO:1). Cleavage sites for BamHI, EcoRI and PstI are indicated. A p53 binding site is indicated in bold.

DETAILED DESCRIPTION OF THE INVENTION

Figure 2:
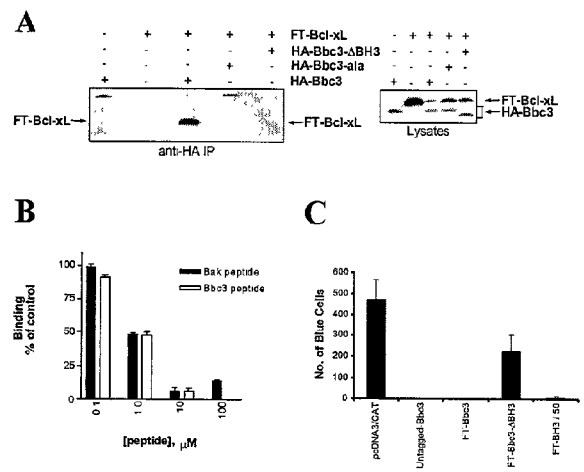
FIG. 2A shows the data from BH3-dependent co-immunoprecipitation of Bbc3 with Bcl-xL. HA-Bbc3 or Bbc3-BH3 mutant constructs were co-transfected with FT-Bcl-xL into Cos7 cells, lysates were immunoprecipitated with anti-HA antibody, and bound Bcl-xL was detected by western blotting with anti-flag antibody (left). Expression of proteins in cell lysates was confirmed by western blotting with anti-HA plus anti-flag antibodies (right).
FIG. 2B shows the results of a competition binding assay where the Bbc3 BH3 domain bound to Bcl-xL. Binding of GST-Bcl-xL to an immobilized Bak BH3 peptide was measured by ELISA (triplicate samples, +S.D.), in the presence of the indicated concentrations of a competing synthetic Bbc3 BH3 or Bak BH3 peptide.
FIG. 2C shows experimental evidence that Bbc3 triggers cell death through its BH3 domain. A control (pcDNA3/CAT) or Bbc3 expression construct was co-transfected with a β-galactosidase marker plasmid into Rat-1 cells. Cell death was measured by the reduction in the number of blue (β-galactosidase expressing) cells 24 hours post-transfection (mean of triplicates, +S.D.).

Technical and scientific terms used herein have the meanings commonly understood by one of ordinary skill in the art to which the present invention pertains, unless otherwise defined.

Reference is made herein to various methodologies known to those of ordinary skill in the art. Publications and other materials setting forth such known methodologies to which reference is made are incorporated herein by reference in their entireties as though set forth in full. Standard reference works setting forth the general principles of recombinant DNA technology include Sambrook, J., et al., *Molecular Cloning,: A Laboratory Manual*, 3d Ed., Cold Spring Harbor Laboratory Press, Cold Spring Harbor, N.Y. (2001); *Directed Mutagenesis: A Practical Approach*, IRL Press, Oxford; Jones, J. (1992); *Amino Acid and Peptide Synthesis*, Oxford Science Publications, Oxford; Austen, B. M. and Westwood, O. M. R. (1991); *Protein Targeting and Secretion*, IRL Press, Oxford. Any suitable materials and/or methods known to those of ordinary skill in the art can be utilized in carrying out the present invention; however, preferred materials and/or methods are described. Materials, reagents and the like to which reference is made in the following description and examples are obtainable from commercial sources, unless otherwise noted.

DESCRIPTION OF THE EMBODIMENTS

Methods for Identifying Compounds that Modulate Apoptosis

The present invention includes methods for identifying compounds that modulate apoptosis.

The first of these methods includes (a) providing a cell containing a polynucleotide encoding a bbc3 gene promoter operably linked to either a bbc3 gene or a reporter gene, (b) exposing the cell to a candidate compound, and (c) determining expression of the bbc3 gene or the reporter gene. A change in the level of expression of the bbc3 gene or the reporter gene is an indication that the candidate compound modulates apoptosis.

The skilled artisan will understand the meaning of the term "apoptosis," but, in general, apoptosis means genetically controlled cell death. Apoptosis is characterized by the condensation of cellular cytoplasm, nuclear fragmentation and migration of nuclear chromatin into discrete masses, mitochondrial and ribosomal compaction, and the dilation of endoplasmic reticulum followed by its fusion with the cell membrane. Finally, the cell breaks apart into several membrane bound vesicles or apoptotic bodies. Activation of particular genes is thought to be necessary before apoptosis can occur. In many organisms, apoptosis is a normal part of morphological development.

According to the present invention, "modulate" apoptosis means to induce apoptosis or inhibit apoptosis. The induction of apoptosis may be less than complete induction of apoptosis. For example, induction can mean the elicitation of apoptotic competency in a cell. Similarly, inhibition of apoptosis can be partial or complete.

According to the present invention, a "compound" that modulates apoptosis means any substance that modulates apoptosis. Such compounds include, but are in no way limited to, chemical or biological compounds including polypeptides, polynucleotides, DNA, RNA, amino acids, and nucleotide compounds, including but not limited to synthetic forms of such compounds, and/or chemically and/or genetically modified forms of such compounds. Suitable polypeptides can include kinases, phosphatases, and other enzymes. A "compound" may be one compound or a combination of two or more compounds.

The skilled artisan will understand that while candidate compounds to be tested in each of the methods of the present invention may be obtained from any source, homologues of known inducers and inhibitors of apoptosis will be promising candidate compounds to be tested. Moreover, sources of compounds include libraries of natural compounds isolated from natural sources, derivatives of such natural compounds, libraries of synthetic chemical compounds, libraries of peptides (synthetic, natural or genetically engineered and produced in a variety of hosts, such as *E. coli*, yeast, mammalian cells and insect cells), libraries of oligo- and poly-nucleotides synthetic, natural or genetically engineered and produced in a variety of hosts, such as *E. coli*.

The term "polypeptide" is used herein as a generic term to refer to an isolated or synthetic full-length protein; or an isolated or synthetic full-length oligopeptide; wherein the protein or oligopeptide has a minimum size of 2 amino acids.

The term "amino acid" is used herein to denote a single amino acid and/or analogs, and/or modified forms thereof.

The term "polynucleotide" is used herein as a generic term to refer to an isolated full-length DNA or RNA; or synthetic full-length DNA and/or RNA; isolated DNA or RNA oligonucleotides; or synthetic DNA and/or RNA oligonucleotides, wherein such a DNA and/or RNA has a minimum size of 2 nucleotides.

The term "nucleotide" is used herein to denote 5'-dNMP, -dNDP, -dNTP, -rNMP, -rNDP, -rNTP; and/or analogs and/or modified forms thereof.

The methods of the present invention can be used to identify compounds that modulate or regulate apoptotic activity and/or anti-apoptotic activity, for example, by inhibiting, diminishing, restoring, or inducing such activity. Such modulation is assayed by using a bbc3 gene promoter operably linked to either the bbc3 gene or a reporter gene.

Under physiological conditions, the bbc3 gene is under control of the bbc3 gene promoter. The skilled artisan will understand that the bbc3 gene promoter includes DNA sequences primarily located upstream of the bbc3 gene, but may also include regions found within introns that occur between the exons that comprise the bbc3 gene, as well as sequences downstream of the bbc3 gene translational stop site. Preferred portions of the human bbc3 gene promoter to be used in each of the methods of the present invention have been identified. They include nucleotides 1934–2099 of the sequence set forth in SEQ ID NO: 1, nucleotides 1168–2099 of the sequence set forth in SEQ ID NO: 1, nucleotides 1–2099 of the sequence set forth in SEQ ID NO: 1, and polynucleotides homologous thereto.

However, the bbc3 gene promoter of any species that has a polynucleotide homologous to that of the human bbc3 gene can be used in the methods of this invention, as can polynucleotides homologous thereto. Alternatively, the bbc3 gene promoter can be a synthetic promoter identical or homologous to the sequences discussed above, designed to have modified activity compared to the naturally occurring promoter.

Polynucleotides are "homologous" to the bbc3 gene if they encode a polypeptide containing a BH3 domain and show substantial sequence identity to the bbc3 gene. Polynucleotides are "homologous" to the bbc3 gene promoter if they encode a polynucleotide that can direct expression of the bbc3 gene or a homologue thereof. With respect to homologues of both the gene and the promoter, their activity need not be quantitatively similar or the same as the wild-type sequence on which they are based. The BH3 domain of a homologous polypeptide need not be identical to the BH3 domain of the Bbc3 protein but may have substantial sequence identity to the Bbc3 protein BH3 domain.

Two polynucleotides share "substantial sequence identity" if the nucleic acids or their complementary strands, when compared, are identical when optimally aligned with appropriate nucleotide insertions or deletions, in at least about 60% of the nucleotides, usually at least about 70%, more usually at least about 80%, preferably at least about 90%, and more preferably at least about 95 to 98% of the nucleotides. Alternatively, substantial sequence identity exists between a first and second polynucleotide when the first polynucleotide will hybridize under selective hybridization conditions, to the second polynucleotide. Selectivity of hybridization exists when hybridization occurs with a certain degree of specificity rather than being random. Typically, selective hybridization will occur when there is at least about 55% identity over a stretch of at least about 14 nucleotides, preferably at least about 65%, more preferably at least about 75%, and most preferably at least about 90%. See, e.g., Kanehisa, *Nuc. Acids Res.*, 12:203–213 (1984).

The skilled artisan will understand how to isolate and prepare a bbc3 gene promoter for use in the methods of the present invention. For example, a bbc3 gene promoter can be isolated by subjecting genomic DNA, isolated from a cell known to express the bbc3 gene, to one or more restriction enzymes. The fragments of genomic DNA can then be subjected to a polymerase chain reaction (PCR) using primers previously identified as bordering a sequence known to function as a bbc3 gene promoter, or a sequence to be tested for its ability to act as a promoter of the bbc3 gene, and PCR products can be isolated.

The bbc3 gene promoter selected for use in the present method is operably linked to the bbc3 gene or a reporter gene. The term "operably" means that expression of the gene is at least under the control of the promoter used in the method.

The present methods can be practiced using the bbc3 gene itself or a reporter gene. If the bbc3 gene is used, candidate compounds are screened for their ability to modulate apoptosis as shown by a change in expression of bbc3 mRNA, a change in expression in Bbc3 protein, or a change in the capacity of Bbc3 for inducing death in a cell.

The skilled artisan will understand that any of a large number of reporter genes can be used in place of, or along with, the bbc3 gene in the present method. Preferably, the reporter gene selected will allow a simple qualitative analysis of whether there is a change in the level of expression of the reporter gene. Preferred reporter genes include a gene encoding a luciferase enzyme, a gene encoding an alkaline phosphatase enzyme, a gene encoding a β-galactosidase enzyme and a gene encoding a chloramphenicol acetyltransferase (CAT) enzyme.

A polynucleotide encoding a bbc3 gene promoter operably linked to a bbc3 gene can be made by inserting both elements into a plasmid expression vector. For example, a polynucleotide sequence encoding a bbc3 gene promoter may be inserted into a plasmid expression vector in its multiple cloning site through the use of restriction enzymes and ligase. A cDNA encoding the bbc3 gene can then be inserted downstream of the bbc3 gene promoter.

A polynucleotide encoding a bbc3 gene promoter operably linked to a reporter gene construct can be made similarly, but using a reporter gene in place of the bbc3 gene.

More than one gene may be included in the expression vector, either as two separate genes, or two genes fused together.

The cells that can be used in the method can be any type of prokaryotic or eukaryotic cell into which foreign pieces of DNA can be transfected and mRNA expressed. Preferably, mammalian cells are used. After construction, the expression vectors are transfected into a chosen cell line using any of the means known to the skilled artisan such as calcium phosphate precipitation, electroporation, and liposomal transfection.

Alternatively, a cell line containing a reporter gene operably linked to a bbc3 gene promoter may be made by "knocking in" a reporter gene through homologous recombination into the bbc3 genomic locus (located on chromosome 19). Methods for knocking in selected genes, such as a reporter gene, are well-known (see, e.g., Hu-Li, et al., *Immunity* 14:1–11 (2001)). Cell lines produced from such a knock in procedure would retain all of the bbc3 regulatory sequences.

Expression of the bbc3 gene or the reporter gene may be determined in any manner for analyzing expression of a gene. Determining includes a qualitative determination of whether the bbc3 gene or a reporter gene is being expressed, and/or whether the level of expression of the bbc3 gene or a reporter gene has changed. The determining may also include any quantitative assay that determines relative or precise levels of expression of the bbc3 gene or a reporter gene. While any indication of expression may be used, preferably the determining is performed by detecting expression of bbc3 mRNA, reporter gene mRNA, Bbc3 protein or reporter gene protein.

Determining conducted by assaying for bbc3 gene mRNA or reporter gene mRNA can be performed by preparing a culture of cells and transfecting a first portion of cells with an expression vector encoding the bbc3 gene or a reporter gene, operably linked to a bbc3 gene promoter. In parallel, as a control a second portion of cells from the same culture is transfected with an "empty" expression plasmid vector which lacks the bbc3 gene or the reporter gene. Both cultures of cells are then treated with a candidate compound. Then, mRNA is isolated from the two cell cultures and relative levels compared, thereby determining expression of the bbc3 gene or the reporter gene.

Determining conducted by assaying for Bbc3 protein or reporter gene protein can be performed as described for mRNA above, but protein is isolated from the two cell cultures, and relative levels compared, such as through western blot analyses. Western blot analyses may be performed using antibodies that recognize the Bbc3 or reporter gene proteins. In addition, epitope tags, such as the influenza hemaglutinin HA tag or the FLAG tag may be linked to the bbc3 gene or the reporter gene, and expression of Bbc3 or reporter gene protein can be determined using anti-HA or anti-FLAG antibodies.

The skilled artisan will also understand how to produce antibodies that recognize the Bbc3 protein or the reporter gene protein. Such antibodies include polyclonal and monoclonal antibodies. The antibodies may be of any class or subclass, and may be whole antibodies, fragments of antibodies, chimeric antibodies from two different species, humanized antibodies, or any other type of antibody that can bind the candidate compound. Anti-HA and anti-FLAG antibodies are commercially available.

Relative protein levels can also be determined without lysing the cultured cells, depending on the particular reporter gene selected. For example, the degree of expression of β-galactosidase in cells transfected with a plasmid expression vector encoding the *E. coli* β-galactosidase gene can be determined by a β-galactosidase ELISA (Boehringer Mannheim), in accordance with the manufacturer's recommendations. Also, the degree of reporter gene activity can be determined by visually scoring, under a microscope, blue cells expressing β-galactosidase, after staining them with X-gal.

In such an assay, a first portion of cells from a culture of cells is transfected with an expression plasmid encoding the β-galactosidase gene operably linked to a bbc3 gene promoter. In parallel, as a control a second portion of cells from the same culture is transfected with an "empty" expression plasmid vector which lacks the reporter gene insert encoding β-galactosidase. Both cultures of cells are then treated with a candidate compound, and the expression of the reporter gene is measured and compared.

The secreted alkaline phosphatase (SEAP) assay system can be used in accordance with the manufacturer's recommendations (Clontech, Palo Alto, Calif.). Use of the luciferase enzyme, the CAT enzyme, and other suitable reporter genes is fully explained in Sambrook, J., et al., *Molecular Cloning, A Laboratory Manual*, Cold Spring Harbor Laboratory Press, Cold Spring Harbor, N.Y., Vol. 3, pp. 17.30–17.47 (2001).

As discussed above, the up-regulation of the bbc3 gene leads to the induction of apoptosis in cells containing the gene. As a result, methods for identifying compounds that modulate apoptosis can also be determined based on the effects of the bbc3 gene expression. For example, the number of cells transfected with an expression vector encoding the bbc3 gene operably linked to a bbc3 gene promoter can be measured after exposure to a candidate compound, with the number of cells remaining stable, increasing, or decreasing, in comparison to the normal cell population. Changes in the apoptotic character of the test cells over the control cells is likely due to changes in the expression of the bbc3 gene. Thus, measurements of the numbers of cells in the two cell cultures is a determining step of the present method.

The degree of cell death or apoptosis can be determined by a variety of methods such as those described in Sellers, J. R., et al., *J. Immunol. Meth.* 172:255–264 (1994) and references cited therein; Telford, W. G., et al., *J. Immunol. Meth.* 172:1–16 (1994) and references cited therein; Poirier, J., Ed. *Apoptosis Techniques and Protocols*, Humana Press, Totowa, N.J. (1997). These methods include Annexin V binding assays, DNA fragmentation assays, assays to detect the activation of caspases, and direct visual scoring of surviving cells under a phase microscope. Indirect assays include measurements of cell viability with a thymidine incorporation assay or an assay based on the cleavage of the tetrazolium salt MMT (3-[4,5-Dimethylthiazol-2-yl]-2,5-diphenyltetrazolium bromide; Thiazolyl blue).

In such an assay, a first portion of cells from a culture of cells is transfected with an expression plasmid encoding the bbc3 gene operably linked to a bbc3 gene promoter. In parallel, as a control a second portion of cells from the same culture is transfected with an "empty" expression plasmid vector which lacks the bbc3 gene. Both cultures of cells are then treated with a candidate compound, and the capacity of Bbc3 for inducing death of the cell is determined. A change in apoptotic activity, i.e., the inhibition or induction of apoptosis, can be detected by comparing the degree of apoptotic activity in the portion of cells transfected with the bbc3 gene to the degree of apoptotic activity detected in the control cells.

Accordingly, the modulatory activity of a candidate compound, i.e., the inhibition or induction of apoptotic activity, can be detected by measuring the relative levels of apoptotic activity exhibited in one portion of a cell culture transfected with an expression vector encoding the bbc3 gene, compared to a second portion of the same cell culture that is transfected with an empty vector (control cells).

While the method can be the three steps set forth above, it can also include additional steps. For example, the method may comprise the additional step of exposing the cells containing the polynucleotide encoding a bbc3 gene promoter operably linked to either a bbc3 gene or a reporter gene to one or more inducers or inhibitors of apoptosis. Based on the components used in the method, and the aims of the method, the cells can be exposed to the one or more inducers or inhibitors at any time during the method, for example, before exposing the cell to the candidate compound, after exposing the cell to the candidate compound or simultaneous with exposure of the cell to the candidate compound.

The inducers or inhibitors may be any of the compounds recited above, as well as others not mentioned and others to be identified in the future, or they may be the absence of any of the compounds recited above. For example, the one or more inducers or inhibitors may be a growth factor or the absence of a growth factor. Also, preferably, the one or more inducers or inhibitors is an agent of DNA damage, a glucocorticoid, p53 or a kinase inhibitor.

The amount of the inducer or inhibitor can be readily determined by the skilled artisan, but in general should be of an amount that produces either a discernable difference in the expression level of the bbc3 gene or reporter gene, or a discernable difference in apoptosis, occurring in a cell culture to which the inducer or inhibitor is applied, as compared to an untreated control culture.

Preferred Methods for Identifying Compounds that Modulate Apoptosis

Preferred versions of the above method for identifying a compound that modulates apoptosis utilize cells in which the activity of the bbc3 gene or the reporter gene is either down-regulated or up-regulated through the addition and/or withdrawal of serum from the culture medium prior to exposure to a candidate compound.

The first preferred method comprises (a) providing a cell containing a polynucleotide encoding a bbc3 gene promoter operably linked to either a bbc3 gene or a reporter gene, (b) culturing the cell in the presence of serum, (c) culturing the cell in the absence of serum, (d) exposing the cell to a candidate compound, and (e) determining expression of the bbc3 gene or the reporter gene. A change in expression is an indication that the candidate compound modulates apoptosis.

This method allows the expression of the bbc3 gene or the reporter gene to first be down-regulated by exposing to serum the cell containing a polynucleotide encoding a bbc3 gene promoter operably linked to either a bbc3 gene or a reporter gene. Removing the serum results in the up-regulation of the gene operably linked to the bbc3 gene promoter chosen in the assay being performed. Thus, ideally the candidate compound down-regulates the gene operably linked to the bbc3 gene promoter, and this method is used to identify compounds that modulate apoptosis through the inhibition of apoptosis.

The second preferred method comprises (a) providing a cell containing a polynucleotide encoding a bbc3 gene promoter operably linked to either a bbc3 gene or a reporter gene, (b) culturing the cell in the presence of serum, (c) culturing the cell in the absence of serum, (d) exposing the cell to a compound known to inhibit bbc3 gene promoter activity, (e) exposing the cell to a candidate compound, and (f) determining expression of the bbc3 gene or the reporter gene. A change in expression is an indication that the candidate compound modulates apoptosis.

This method allows the expression of the bbc3 gene or the reporter gene first to be down-regulated by exposing to serum the cell containing a polynucleotide encoding a bbc3 gene promoter operably linked to either a bbc3 gene or a reporter gene. Removing the serum results in the up-regulation of the gene operably linked to the bbc3 gene promoter chosen in the assay being performed. Exposure of the cells to a known inhibitor of bbc3 gene promoter activity results in down-regulation of the gene. Thus, ideally the candidate compound up-regulates the gene operably linked to the bbc3 gene promoter, and this method is used to identify compounds that modulate apoptosis through induction of apoptosis.

The skilled artisan will understand that the culture medium utilized in both of these methods depends on the cell type selected for use in the method. The serum used in the methods may be whatever type of serum generally is used to culture the selected cell type. Similarly, the concentration of serum used in the culture medium is that which is generally used to culture the selected cell type. Serum such as fetal bovine serum, bovine newborn calf serum, bovine calf serum, and human serum are acceptable.

Unless otherwise indicated, each of the terms, components and steps for the preferred methods is the same as those described above for the general method of identifying compounds that modulate apoptosis.

Each of the methods described above can be used to identify compounds that modulate apoptosis by directly contacting the bbc3 gene promoter being used in the assay. However, compounds can also be identified that interact with a component of the apoptotic pathways in which the bbc3 gene is involved, both up-stream and down-stream of the function of the Bbc3 protein. The methods can be used to identify compounds that down-regulate apoptosis in a cell, as well as a compounds that up-regulate apoptosis in a cell.

Because bbc3 appears to be subject to transcriptional regulation by multiple cell death signaling pathways, the methods of the present invention can be utilized to identify compounds that influence a number of different cell death signaling pathways.

Methods for Identifying Compounds that Modulate bbc3 Gene Expression

Three other methods of the present invention are analogous to those methods described above for identifying compounds that modulate apoptosis, except that they are methods for identifying compounds that modulate expression of the bbc3 gene.

The first method for identifying a compound that modulates bbc3 gene expression comprises (a) providing a cell containing a polynucleotide encoding a bbc3 gene promoter operably linked to either a bbc3 gene or a reporter gene, (b) exposing the cell to a candidate compound, and (c) determining expression of the bbc3 gene or the reporter gene. A change in expression of the gene is an indication that the candidate compound modulates bbc3 gene expression.

As with the first method described above for identifying compounds that modulate apoptosis, there are preferred embodiments of this method of identifying compounds that modulate bbc3 gene expression where expression of the bbc3 gene or the reporter gene is first down-regulated or up-regulated.

The first preferred method for identifying a compound that modulates bbc3 gene expression comprises (a) providing a cell containing a polynucleotide encoding a bbc3 gene promoter operably linked to either a bbc3 gene or a reporter gene, (b) culturing the cell in the presence of serum, (c) culturing the cell in the absence of serum, (d) exposing the cell to a candidate compound, and (e) determining expression of the bbc3 gene or the reporter gene. A change in expression is an indication that the candidate compound modulates bbc3 gene expression.

This method allows the expression of the bbc3 gene or the reporter gene to first be down-regulated by exposing the cell containing a polynucleotide encoding a bbc3 gene promoter operably linked to either a bbc3 gene or a reporter gene to serum. Removing the serum results in the up-regulation of the gene operably linked to the bbc3 gene promoter chosen in the assay being performed. Thus, ideally the candidate compound down-regulates the gene operably linked to the bbc3 gene promoter, and this method is used to identify compounds that modulate bbc3 gene expression through the inhibition of such expression.

The second preferred method for identifying a compound that modulates bbc3 gene expression comprises (a) providing a cell containing a polynucleotide encoding a bbc3 gene promoter operably linked to either a bbc3 gene or a reporter gene, (b) culturing the cell in the presence of serum, (c) culturing the cell in the absence of serum, (d) exposing the cell to a compound known to inhibit bbc3 gene promoter activity, (e) exposing the cell to a candidate compound, and (f) determining expression of the bbc3 gene or the reporter gene. A change in expression is an indication that the candidate compound modulates bbc3 gene expression.

This method allows the expression of the bbc3 gene or the reporter gene to first be down-regulated by exposing the cell containing a polynucleotide encoding a bbc3 gene promoter operably linked to either a bbc3 gene or a reporter gene to serum. Removing the serum results in the up-regulation of the gene operably linked to the bbc3 gene promoter chosen in the assay being performed. Exposure of the cells to a known inhibitor of bbc3 gene promoter activity results in the down-regulation of the gene. Thus, ideally the candidate compound up-regulates the gene operably linked to the bbc3 gene promoter, and this method is used to identify compounds that modulate bbc3 gene expression through the induction of such expression.

In a fourth method for identifying a compound that modulates bbc3 gene expression the method comprises (a) providing a composition comprising a polynucleotide encoding a bbc3 gene promoter operably linked to either a bbc3 gene or a reporter gene, (b) exposing the composition to a candidate compound, and (c) determining expression of the bbc3 gene or the reporter gene. A change in expression is an indication that the candidate compound modulates bbc3 gene expression.

This method can be used to identify both compounds that inhibit bbc3 gene expression, and those that induce bbc3 gene expression. Preferably, this method is performed in a cell-free or in vitro environment, such as by an in vitro transcription assay.

In vitro transcription assays can be carried out using nuclear extracts from mammalian cells or tissues, and measuring transcription directed by the bbc3 gene promoter by quantitative PCR, primer extension analysis, or incorporation of radioactive ATP, UTP, CTP or GTP. Such methods for in vitro transcription assays are described in M. Carey, et al., *Transcriptional Regulation in Eukaryotes: Concepts Strategies and Techniques*, Cold Spring Harbor Laboratory Press; Cold Spring Harbor, N.Y., Chapter 14, Crude and Fractionated Systems for In Vitro Transcription, pp. 505–579 (2000).

Unless otherwise indicated, each of the terms, components and steps is the same as those described above for the methods of identifying compounds that modulate apoptosis.

Method for Identifying Compounds that Interact with a bbc3 Gene Promoter

The present invention also includes a method for identifying a compound that interacts with a bbc3 gene promoter. The method comprises (a) providing a bbc3 gene promoter, (b) contacting the promoter with a candidate compound, and (c) detecting an interaction between the promoter and the candidate compound, thereby identifying a compound that interacts with the bbc3 gene promoter.

The "detecting" of an interaction between a bbc3 gene promoter and a candidate compound can be performed by a variety of methods well-known to the skilled artisan. Preferably, the detecting is performed using an antibody that recognizes and binds a candidate compound, performed using polymerase chain reaction or performed by gel retardation analysis.

The detecting performed using an antibody includes, but is not limited to, western blot analyses and immunoprecipitation.

The detecting performed using the polymerase chain reaction (PCR) can be a simple assay where the lack of a PCR product can indicate that the bbc3 gene promoter being assayed was bound by the candidate compound and interfered with the polymerase included in the PCR reaction system. Other means by which PCR may be used in this method will be readily apparent to the skilled artisan.

The detecting performed by gel retardation analysis indicates that a candidate compound is bound to the bbc3 gene promoter being assayed because a sample applied to the gel that includes a candidate compound and the promoter moves more slowly through a gel system than a control sample which contains the promoter alone (Sambrook, J., et al., *Molecular Cloning, A Laboratory Manual*, Cold Spring Harbor Laboratory Press, Cold Spring Harbor, N.Y., Vol. 3, pp. 17.13–17.16 (2001)).

While the present method can be performed in a cell-free system, preferably the bbc3 gene promoter being assayed is in a cell and the cell is contacted with the candidate compound.

Unless otherwise indicated, each of the terms, components and steps is the same as those described above for the methods of identifying compounds that modulate apoptosis.

Method for Modulating Apoptosis

The present invention also includes a method for modulating apoptosis. The method comprises (a) providing a cell containing the bbc3 gene operably linked to a bbc3 gene promoter, and (b) contacting the cell with a compound identified in any of the methods discussed above for identifying compounds that modulate apoptosis.

While any degree of modulation of apoptosis is contemplated by this method, preferably the modulating inhibits or induces apoptosis in a cell.

Method for Modulating bbc3 Gene Expression

Similarly, the present invention also includes a method for modulating bbc3 gene expression. This method comprises (a) providing a cell containing the bbc3 gene operably linked to a bbc3 gene promoter, and (b) contacting the cell with a compound identified in any of the methods discussed above for identifying a compound that modulates bbc3 gene expression.

While any degree of modulation of bbc3 gene expression is contemplated by this method, preferably the modulating inhibits or induces bbc3 gene expression.

Unless otherwise indicated, each of the terms, components and steps is the same as those described above for the methods of identifying compounds that modulate apoptosis.

Method for Making a Compound

The present invention also includes a method for making a modulator of apoptosis. The method comprises (a) carrying out any of the methods described herein for identifying a modulator of apoptosis, thereby identifying a compound that is a modulator of apoptosis, and (b) manufacturing the compound.

Similarly, the present invention includes a method for making a modulator of bbc3 gene expression. The method comprises (a) carrying out any of the methods described herein for identifying a modulator of bbc3 gene expression, thereby identifying a compound that is a modulator of bbc3 gene expression, and (b) manufacturing the compound.

Unless otherwise indicated, each of the terms, components and steps is the same as those described above for the methods of identifying compounds that modulate apoptosis.

Compound

The present invention is also directed to compounds identified by any of the methods described herein.

Promoter

Finally, the present invention includes isolated nucleic acid molecules. Preferably, the nucleic acid molecules are the polynucleotide sequence of bases 1–2099 of SEQ ID NO: 1, the polynucleotide sequence of bases 1168–2099 of SEQ ID NO: 1, and the polynucleotide sequence of bases 1934–2099 of SEQ ID NO: 1.

The isolated nucleic acid molecules may also be polynucleotides homologous to the polynucleotide sequence of bases 1–2099 of SEQ ID NO: 1, polynucleotides homologous to the polynucleotide sequence of bases 1168–2099 of SEQ ID NO: 1, and polynucleotides homologous to the polynucleotide sequence of bases 1934–2099 of SEQ ID NO: 1. The meaning of the term "homologous" is as described above.

EXAMPLES

Example 1

Discovery of a Novel BH3-only, Pro-Apoptotic Protein

A yeast two-hybrid interaction screen was carried out using Bcl-2 as bait to identify cellular proteins that bind to Bcl-2. Three classes of strongly interacting clones were isolated by screening a human lymphocyte cDNA library: two were cDNA clones encoding Bik and Bad, previously identified BH3-only proteins that bind to Bcl-2, and the third was a novel gene, designated bbc3, for Bcl-2 binding component 3. This bbc3 cDNA sequence was originally deposited in GenBank in 1997 (accession no. U82987), but was annotated at that time with a deduced amino acid sequence in a +1 register relative to the correct Bbc3 open reading frame.

Bbc3 was found to interact with the Bcl-2 related cell death suppressor, Bcl-xL, but not with the pro-apoptotic proteins Bik and Bak in the two-hybrid assay. The bbc3 cDNA encodes a protein of 193 amino acids that harbors a candidate BH3 domain (FIG. 1A) that shares the most similarity to Egl-1 and Bad. Several residues immediately adjacent to the more highly conserved core BH3 residues are identical in Bbc3 and Egl-1 (FIG. 1B). Murine Bbc3 shares greater than 90% overall amino acid identity with human Bbc3, including perfect conservation within the BH3 regions.

Bbc3 was found to exhibit functional properties that define BH3-only proteins. Immunofluorescence and cell fractionation studies demonstrated that Bbc3 localizes to mitochondrial membranes, as has been described for other BH3-only proteins (Huang, D. C., et al., Cell 103:839–42 (2000)). In transiently transfected cells, an HA epitope-tagged form of Bbc3 co-immunoprecipitated with Flag epitope-tagged Bcl-xL (FIG. 2A), confirming that Bbc3 can bind to Bcl-xL in mammalian cells.

Alanine substitution of three conserved residues within the BH3 domain of Bbc3 (HA-Bbc3ala), or a 10 amino acid deletion within BH3 (HA-Bbc3ΔBH3), destroyed the ability of Bbc3 to bind to Bcl-xL both in transfected cells (FIG. 2A) and in vitro. Competition binding assays demonstrated that a 20 amino acid synthetic peptide encompassing the Bbc3 BH3 domain (residues 133 to 152) bound to recombinant GST-Bcl-xL in vitro with an affinity comparable to a previously characterized Bak BH3 peptide (Zhou, X. M., et al., J. Biol. Chem. 275:25046–51 (2000)) (FIG. 2B). Therefore, the BH3 domain of Bbc3 is both necessary and sufficient for binding to Bcl-xL.

Previously characterized BH3-only proteins exhibit pro-apoptotic activity that is dependent, at least in part, on their respective BH3 domains (Huang, D. C., et al., Cell 103: 839–42 (2000)). To test the ability of Bbc3 to induce apoptosis, untagged and Flag-epitope tagged Bbc3 (FT-Bbc3) expression plasmids were transiently co-transfected with a β-galactosidase marker plasmid into Rat-1 cells (FIG. 2C). Bbc3 showed remarkably potent cell death-promoting activity in this assay, as detected by the almost complete elimination of β-gal-marked cells at 24 hours post-transfection (FIG. 2C) in comparison to 400–500 β-gal-marked cells observed with the control plasmid (pcDNA3/CAT). Deletion of BH3 domain residues reduced, but did not completely eliminate, the cell killing activity of Bbc3 (FT-Bbc3ΔBH3) (FIG. 2C). Also, a truncated form of Bbc3 comprising 50 amino acids of the BH3 region (residues 136–185), retained significant pro-apoptotic function (FT-BH3/50) (FIG. 2C). The pro-apoptotic activity of Bbc3 in this assay could be suppressed by co-transfection with a dominant-negative form of caspase-9 or Bcl-xL at high molar ratio (not shown). Together, the BH3-dependent dimerization and pro-apoptotic activities of Bbc3 indicate that it functions in a mechanistically similar fashion to previously characterized BH3-only proteins.

Experiment 2

Bbc3 mRNA Levels are Induced by DNA Damage and p53

To evaluate whether the activity of bbc3 might be under transcriptional control, the expression of bbc3 was examined in response to apoptotic stimuli likely to involve new mRNA/protein synthesis. Exposure of murine NIH3T3 cells to the DNA-damaging drug etoposide, led to the rapid induction of bbc3 mRNA levels (FIG. 3A), prior to the onset of apoptosis.

Figure 3:
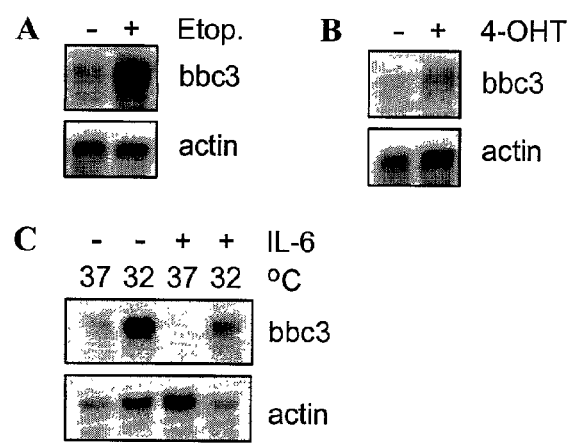
FIG. 3 shows the induction of bbc3 mRNA by p53. Northern blots were hybridized with a murine bbc3 cDNA probe, followed by re-hybridization with an actin probe.

Cell death induced by etoposide and other DNA-damaging drugs in murine fibroblasts is mediated, at least in part, by the p53 tumor suppressor (Levine, A. J., Cell 88:323–31 (1997); Vousden, K. H., Cell 103:691–4 (2000)). Therefore, it was determined whether p53 was sufficient to induce bbc3 mRNA levels, using cell lines with conditional p53 function. Wild-type p53 activity can be specifically induced by the addition of 4-hydroxytamoxifen (4-OHT) to E1a/Ras transformed p53−/− mouse embryo fibroblasts that express a p53-estrogen receptor fusion protein (Vater, C. A., et al., Oncogene 13:739–48 (1996)). Activation of p53 by exposure to 4-OHT in these cells, was sufficient to induce bbc3 mRNA levels, preceding the onset of cell death (FIG. 3B).

A second cell line, murine M1p53ts cells, expresses a temperature sensitive mutant p53, that is inactive at 37° C. but assumes wild-type conformation and activity at 32° C. (Yonish-Rouach, E., et al., Nature 352:345–7 (1991)). Bbc3 mRNA levels were significantly induced following wild-type p53 activation by temperature shift to 32° C. (FIG. 3C). IL-6, which suppresses apoptosis induced by p53 in M1 cells (Yonish-Rouach, E., et al., Nature 352:345–7 (1991)), did not prevent induction of bbc3 mRNA at 32° C. (FIG. 3C). Thus, wild-type p53 was shown to be sufficient to induce bbc3, and elevated bbc3 levels are not a response to the onset of cell death, per se.

Experiment 3

Bbc3 is a Direct Transcriptional Target of p53

Considering the rapid activation of bbc3 mRNA by p53, it was determined whether p53 acts directly on the bbc3 gene promoter. Comparison of the bbc3 cDNA to the draft human genome sequence indicated that the bbc3 gene is comprised of 4 exons on chromosome 19 (accession number AC008532). P1 genomic DNA clones encompassing the bbc3 gene were isolated, and DNA segments encoding exon 1 and sequences immediately 5' to exon 1 were characterized by subcloning and DNA sequence analysis. Notably, a DNA sequence motif that is an excellent match to the consensus DNA binding site defined for p53 (el-Deiry, W. S., et al., Nat. Genet. 1:45–9 (1992)) was identified 150 bp upstream of the 5' end of the bbc3 cDNA (FIG. 4A) and is conserved in the mouse bbc3 genomic locus (accession no. AC073741).

To test whether this candidate bbc3 gene promoter region is transactivated by p53, genomic DNA segments encompassing either 2.0, 0.9 or 0.17 kb of DNA sequences immediately 5' to bbc3 exon 1 (FIG. 4A), were subcloned into the promoter-less luciferase reporter vector, pGL3. Each of these constructs containing the predicted p53 binding site element was strongly transactivated by co-transfection with a plasmid encoding wild-type p53 in p53-deficient Saos-2 cells (FIG. 4B). No transactivation was detected upon co-transfection with a plasmid expressing a mutant p53 that is defective for transactivation function (FIG. 4B).

To determine whether the putative p53 binding site mediates transactivation of the bbc3 gene promoter by p53, four single nucleotide substitution mutations were introduced to eliminate its potential recognition by p53 (shown in FIG. 4A). While the 0.9 kb bbc3 gene promoter region with the unaltered p53 binding site was strongly transactivated, the same 0.9 kb region harboring the mutated site failed to be transactivated by wild-type p53 (pGL3/0.9mut) (FIG. 4C).

These results demonstrate bbc3 is a direct target for p53 transactivation through a p53 binding site within the bbc3 gene promoter region.

Experiment 4

Glucocorticoid Treatment and Serum Deprivation Also Induce Bbc3

Figure 5:
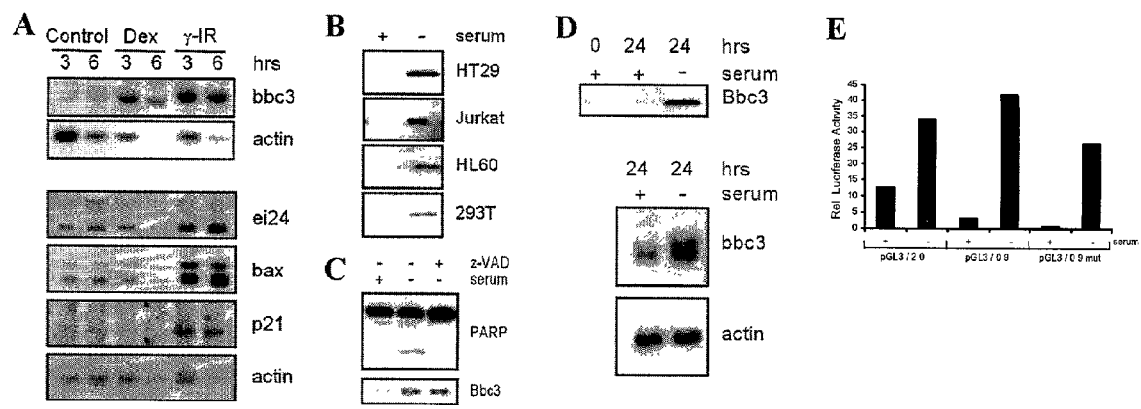
FIG. 5A shows the results of a northern blot analysis of primary murine thymocytes treated with 1 μM dexamethasone (Dex) or 5 Gy ionizing radiation (γ-IR). RNA samples were prepared 3 or 6 hours after treatment and mRNA for bbc3 and actin was detected by sequential probing of the northern blot (top 2 panels). A separate blot prepared from the same RNA samples was probed for ei24, bax, p21, and actin, sequentially (bottom 4 panels).
FIG. 5B shows an immunoblot analysis of Bbc3 protein expression in human tumor cell lines, cultured in the presence or absence of serum for 24 hrs.
FIG. 5C shows the data from Jurkat cells cultured in media without serum for 24 hrs, in the absence or presence of the caspase inhibitor z-VAD (100 μM). Bbc3 and PARP were detected by western blot analysis.
FIG. 5D shows the data from HT29 cells grown in the presence of serum (time 0) and incubated in the presence (+) or absence (−) of serum for 24 hrs. Bbc3 protein was detected by western analysis (top) and mRNA expression was detected by northern analysis (bottom panels).
FIG. 5E shows results from the activation of the bbc3 gene promoter by serum withdrawal. The indicated bbc3 gene promoter luciferase reporter plasmids were transfected into HeLa-Bcl-xL cells. At 24 hours after transfection, cells were incubated for an additional 24 hrs in the presence of 20% serum (+) or absence of serum (−). Luciferase activity was measured and normalized for transfection efficiency.

It was shown that a broader range of apoptotic stimuli can regulate bbc3 expression, including cell death pathways that are not mediated by p53. In primary murine thymocytes, exposure to ionizing radiation triggered apoptosis through a p53-dependent pathway, whereas treatment with the glucocorticoid dexamethasone induced rapid cell death through a p53-independent pathway (Lowe, S. W., et al., *Nature* 362: 847–9 (1993); Clarke, A. R., et al., *Nature* 362:849–52 (1993)). Consistent with our finding that bbc3 is a direct p53 target, γ-irradiation of thymocytes led to the induction of bbc3 mRNA in parallel with the mRNAs for the previously characterized p53 targets, ei24 (Gu, Z., et al., *Mol. Cell. Biol.* 20:233–41 (2000)), bax (Miyashita, T., et al., *Cell* 80:293–9 (1995)), and p21 (el-Deiry, W. S., et al., *Cell* 75:817–25 (1993)) (FIG. 5A). Significantly, treatment of thymocytes with dexamethasone also induced bbc3 mRNA expression, in marked contrast to the other p53 target genes (FIG. 5A). Thus, bbc3 mRNA levels can be induced in the same cell type by both p53-dependent and p53-independent cell death pathways.

Deprivation of serum is a strong pro-apoptotic stimulus for many cultured tumor cell lines, triggering cell death or sensitizing cells to other apoptotic stimuli. Thus, the effect of serum deprivation on bbc3 mRNA expression and Bbc3 protein levels was also examined, using a monoclonal antibody generated against recombinant human Bbc3. A striking increase in Bbc3 protein levels was observed upon serum deprivation in multiple human tumor cell lines (FIG. 5B), including cell lines that lack functional p53. Addition of the broad-spectrum caspase inhibitor, z-VAD, to serum-starved Jurkat cells, prevented cleavage of the caspase substrate, PARP, but had no impact on the induction of Bbc3 protein levels (FIG. 5C). Therefore, the induction of Bbc3 precedes caspase activation, and is not simply a response to the engagement of the cell death program.

In the human colon cancer cell line HT29, a dramatic increase in Bbc3 protein levels was observed 24 hours after serum withdrawal (FIG. 5D, top panel). Elevation of Bbc3 protein levels was observed within 4 hours after serum withdrawal in these cells, whereas levels of other Bcl-2 and BH3-only family members tested, including Bax, Bcl-xL, Bak, Bid and Bad, were not induced by serum withdrawal (not shown). Coordinate changes in bbc3 mRNA levels were observed (FIG. 5D, bottom), suggesting that the elevation of Bbc3 expression by serum deprivation occurs principally at a transcriptional level.

To further define the mechanisms by which growth factors control bbc3 expression, the bbc3 gene promoter region was tested to determine whether it directly responds to serum deprivation. Bbc3 gene promoter/luciferase reporter constructs were tested for their activity in transfected HeLa/Bcl-xL cells, cultured in either the presence or absence of serum. HeLa/Bcl-xL cells were used in these experiments because of their relatively high transfection efficiency, and because Bcl-xL expression prevents high levels of cell death that otherwise occur after serum withdrawal. Luciferase reporter constructs containing 2.0 kb and 0.9 kb of the bbc3 gene promoter region were both significantly activated when transfected cells were cultured in serum-free conditions (FIG. 5E). By contrast, the activity of a pGL3/SV40 promoter control luciferase construct was reduced significantly in the absence of serum, representing a more typical response of promoters to serum deprivation. Mutation of the p53 binding site in the bbc3 gene promoter region did not prevent activation by serum withdrawal (pGL3/0.9 mut; FIG. 5E), confirming that this effect does not require p53.

These findings indicate that the bbc3 gene promoter region is activated in response to serum deprivation, and provide further evidence that growth factors control bbc3 gene expression at a transcriptional level.

Experiment 5

Growth Factors with Anti-Apoptotic Activity Suppress Bbc3 Expression

Figure 6:
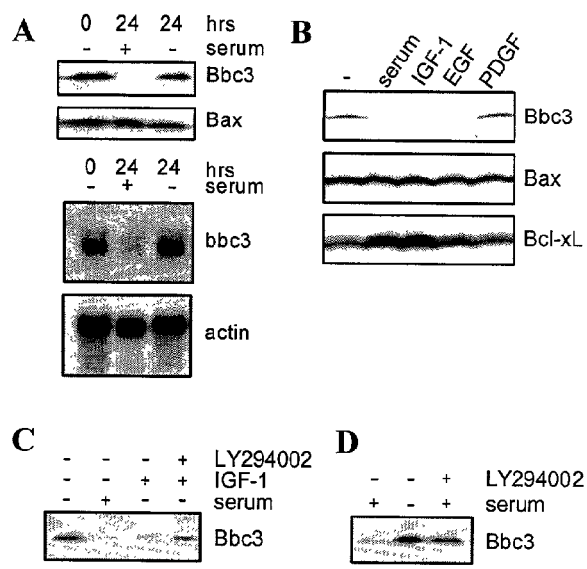
FIG. 6A shows that serum represses the expression of Bbc3. HT29 cells were incubated for one day in the absence of serum (time 0), and then cultured in the presence (+) or absence (−) of serum for 24 hrs. Bbc3 protein was detected by western blot, with an additional probing of the blot for Bax expression (top 2 panels); bbc3 mRNA levels were detected by Northern analysis (bottom 2 panels).
FIG. 6B shows that anti-apoptotic growth factors repress the expression of Bbc3. HT29 cells were incubated for one day in the absence of serum (−), and then incubated in media containing either serum, 100 ng/ml IGF-1, 50 ng/ml EGF, or 25 ng/ml PDGF, for 24 hrs. Bbc3 was detected by western blot analysis, followed by sequential probing of the blot with anti-Bax and anti-Bcl-xL antibodies.
FIG. 6C shows that the PI-3 kinase specific inhibitor, LY294002, impairs the ability of the IGF-1 to suppress the expression of Bbc3. HT29 cells were cultured as in FIG. 6B and then incubated for 24 hrs in media containing either serum, 100 ng/ml IGF-1, or 100 ng/ml IGF-1 in the presence of 50 μM LY294002 (added 1 hr prior to IGF-1). Bbc3 was detected by western blot analysis.
FIG. 6D shows that the PI-3 kinase specific inhibitor, LY294002, impairs the ability of serum to suppress the expression of Bbc3. HT29 cells were grown in the presence of serum (lane 1), and then incubated for 24 hrs in the absence of serum, or in the presence of serum supplemented with 50 μMLY294002.

The increase in Bbc3 caused by serum withdrawal in HT29 cells was 'reversible' in that Bbc3 protein levels were markedly reduced 24 hours after the re-addition of serum (FIG. 6A, top panels), which correlated with changes in bbc3 mRNA levels (FIG. 6A, bottom panels).

The influence of serum on Bbc3 expression led to further tests to determine whether the addition of specific growth factors would be sufficient for suppressing Bbc3 levels. Addition of either IGF-1 or EGF, growth factors with broad anti-apoptotic activity, strongly inhibited Bbc3 protein expression in serum-starved HT29 cells (FIG. 6B), while having no effect on Bax or Bcl-xL. A third growth factor, PDGF, failed to suppress Bbc3 levels in this assay, however, it was not determined if PDGF receptors are expressed and activated by PDGF in HT29 cells.

In many settings, anti-apoptotic signaling by the IGF-1 receptor requires the activation of phosphatidylinositol-3 kinase (PI-3 kinase) (Dudek, H., et al., *Science* 275:661–5 (1997); O'Connor, R., et al., *Biochem. Soc. Trans.* 28:47–51 (2000)). Addition of the PI-3 kinase specific inhibitor, LY294002, impaired the ability of IGF-1 to suppress Bbc3 levels in serum-starved HT29 cells (FIG. 6C). LY294002 treatment also significantly impaired the ability of serum to suppress Bbc3 protein levels in the same context (FIG. 6D), suggesting that PI-3 kinase is required for serum and IGF-1 to suppress expression of Bbc3. Together, these results raise the possibility that suppression of bbc3, a strongly pro-apoptotic BH3-only gene, is an important component of anti-apoptotic signaling by growth factor receptors.

Addition of the EGF receptor kinase inhibitor AG1478 blocked the ability of EGF and serum to suppress Bbc3 protein expression in HT29 cells (FIGS. 7A and 7B). The mitogen-activated protein kinase kinase (MAPKK) inhibitor, PD98059, and the tyrosine kinase inhibitor, tyrphostin AG1024, also impaired the ability of serum to suppress Bbc3 protein expression (FIG. 7B). Thus, Bbc3 protein levels respond to a diversity of chemical inhibitors of signal transduction pathways that are important to cell survival.

Experiment 6

Cell Survival Signal Transduction Pathways Control the Activity of the Bbc3 Gene Promoter Additional experiments were performed to determine whether the bbc3 gene promoter was regulated by signal transduction pathways known to play a role in cell survival. A bbc3 gene promoter-luciferase reporter construct containing 0.9 kb of the bbc3 gene promoter region, was transfected into HeLa/Bcl-xL cells and the activity of the promoter measured by luciferase assays 48 hours after transfection. Consistent with the data presented above (FIG. 4E), the levels of luciferase activity were induced significantly when transfected cells were cultured in the absence of serum (FIG. 8A). The induction of bbc3 gene promoter activity in the absence of serum was substantially reduced by the addition of IGF-1, suggesting that the effect of IGF-1 on Bbc3 protein levels (e.g. FIG. 6B, 6C) occurs through a transcriptional mechanism. Addition of the PI-3 kinase inhibitor, Ly294002, to transfected cells cultured in the presence of serum, was sufficient to induce activity of the bbc3 gene promoter (FIG.

8A). Thus, a PI-3 kinase dependent pathway controls, at least in part, the activity of the bbc3 gene promoter.

An important downstream effector of the PI-3 kinase-mediated cell survival pathway is the serine/threonine kinase, Akt (Dudek, H., et al., *Science* 275:661–5 (1997); O'Connor, R., et al., *Biochem. Soc. Trans.* 28:47–51 (2000)). Co-transfection of the 0.9 kb bbc3 gene promoter reporter construct with a plasmid expressing a dominant negative form of PI-3 kinase (PI3k-DN), was sufficient to induce bbc3 gene promoter activity, even in the presence of serum (FIG. 8B). Conversely, co-transfection of the reporter with a constitutively active form of Akt (pM-AKT) was sufficient to suppress bbc3 gene promoter activity when cells were cultured in the absence of serum. These results demonstrate that the activity of the bbc3 gene promoter responds to molecules that influence cell survival signaling pathways.

Materials and Methods

Isolation of a bbc3 cDNA

A 1.6 kb bbc3 cDNA encoding the full length Bbc3 open reading frame (accession no. U82987) was isolated in a yeast two hybrid screen using a GAL4 DNA-binding domain/Bcl-2 fusion protein and a human lymphocyte cDNA library (Matchmaker system, Clontech). Analysis of a homologous human EST (accession no. AI784404) identified additional 5' untranslated sequences, yielding an assembled 1.9 kb cDNA that matches the bbc3 message size detected by northern analysis. A cDNA encoding the murine Bbc3 open reading frame was isolated by PCR using cDNA from M1p53ts cells.

Cell Lines

All cell lines used were obtained from ATCC, unless otherwise noted. HeLa/Bcl-$X_L$ cells were generated by stable transfection of HeLa cells with a vector encoding a Flag-epitope tagged BCl-$x_L$. Murine myeloid leukemia M1 cells containing a temperature sensitive p53-val135 mutant (M1p53ts), and E1A/ras transformed p53−/−mouse embryonic fibroblasts containing a p53-estrogen receptor fusion, have been described previously (Vater, C. A., et al., *Oncogene* 13:739–48 (1996); Yonish-Rouach, E., et al., *Nature* 352:345–7 (1991)).

Plasmid Constructs and Cell Death Assays

The 1.6 kb bbc3 cDNA was subcloned into the pcDNA3 vector (Invitrogen) for expression of an untagged form of Bbc3. The Bbc3 open reading frame was amplified by PCR and cloned into pcDNA3, incorporating either an amino terminal influenza hemaglutinin tag (HA) or Flag epitope tag (FT). Oligonucleotide-directed mutagenesis was used to introduce alanine substitutions at amino acids 141, 144, and 147, to generate the pcDNA3/HA-Bbc3-ala plasmid. Amino acids 141–150 were deleted to generate both HA and FT forms of Bbc3-ΔBH3 in pcDNA3, and a bbc3 segment encoding amino acids 136–185 was amplified by PCR and cloned into pcDNA3 to generate the FT-BH3/50 construct. All Bbc3 constructs were verified by DNA sequencing. The effect of Bbc3 expression on cell viability was tested in Rat-1 cells using a transient transfection assay, as previously described (Chittenden, T., et al., *EMBO J.* 14:5589–96 (1995)).

Binding Assays

Cos7 cells were transiently transfected with HA-Bbc3 and FT-Bcl-$x_L$ expression plasmids, following the lipofectamine procedure (Gibco/BRL). Cell lysates were prepared and co-immunoprecipitation assays were performed as described previously (Chittenden, T., et al., *EMBO J.* 14:5589–96 (1995)). The Bcl-$x_L$ competition binding assay was performed as previously described (Zhou, X. M., et al., *J. Biol. Chem.* 275:25046–51 (2000)), using synthetic BH3 peptides comprising residues 133–152 of Bbc3, and residues 70–89 of Bak.

Generation of a Bbc3 Monoclonal Antibody and Western Blot Analysis

A mouse monoclonal antibody, KM140, was made against a recombinant GST-Bbc3 fusion protein. The KM140 epitope was mapped to residues 73–76 by probing a blot with arrayed overlapping Bbc3 peptides (Research Genetics). Cells were plated at 3–10×10$^6$ cells per 100 mm dish in either serum containing (10% FBS), or serum free media (0% FBS, 0.1% BSA). Cell lysates were prepared, electrophoresed (100 to 200 μg per lane) on 4–20% polyacrylamide reducing gels, and analyzed by western blotting as described previously (Chittenden, T., et al., *EMBO J.* 14:5589–96 (1995)).

Northern Blot Analysis

Total RNA was isolated from mouse thymocytes (RNeasy system, Qiagen). Poly(A)+RNA (FastTract system, Invitrogen) was prepared in all other experiments. 10 μg of total RNA or 3 μg of poly(A)+RNA per lane was denatured and separated by electrophoresis in 1% formaldehyde agarose gels. Northern blotting was performed following standard methods.

Bbc3 Reporter Constructs and Luciferase Reporter Assay

A human P1 genomic DNA library (Genome Systems) was screened with a 5' end-bbc3 cDNA PCR product, yielding two P1 bbc3 genomic DNA clones. A 2.0 kb BamHI genomic DNA fragment immediately upstream of the 5' end of bbc3 cDNA was identified by southern blot analysis, subcloned and sequenced. The 3' BamHI site present in the 2.0 kb fragment is located 35 bp upstream of the 5' end of the 1.9 kb bbc3 cDNA. The 2.0 kb BamHI fragment, representing the candidate bbc3 gene promoter region, was cloned into the pGL3Luc-Basic luciferase reporter vector (Promega) to generate pGL3/2.0. Unique EcoRI and PstI sites within the 2.0 kb fragment yielded a 0.9 kb EcoRI/BamHI fragment and a 0.17 kb PstI/BamHI fragment, which were cloned into pGL3Luc-Basic to generate pGL3/0.9 and pGL3/0.17, respectively. Nucleotide substitutions were introduced into the putative p53 binding site in pGL3/0.9 by oligonucleotide-directed mutagenesis, to generate pGL3/0.9mut.

Luciferase assays were performed using the Dual-Light System (Tropix) for the combined detection of luciferase and β-galactosidase. Saos-2 cells were transfected with Superfect (Qiagen) in 6 well plates using 1.8 μg luciferase reporter plasmid, and 0.025 μg of pRC/CMV encoding either wild type p53 or mutant p53-SN22/23 (Lin, J., et al., *Genes Dev.* 8:1235–46 (1994)). The β-galactosidase reporter pCMVβ-gal (Promega) was included (0.1 μg) as an internal control for transfection efficiency. Luciferase and β-galactosidase activities were measured 24 hours following transfection. Transfections of HeLa/Bcl-xL cells were performed in 6 well plates using 1.8 μg luciferase reporter plasmid and 0.1 μg pCMVβ-gal. Cell culture medium was changed to either DMEM containing 20% serum, or DMEM without serum, 24 hours following transfection and luciferase/β-galactosidase levels were measured after an additional 24 hours of incubation. All reporter assays yielded similar results in at least three independent experiments.

While the invention has been described in detail and with reference to specific embodiments thereof, it will be apparent to one skilled in the art that various changes and modifications can be made therein without departing from the spirit and scope thereof.

What is claimed is:

1. A method for identifying a compound that modulates apoptosis, the method comprising:
   a. providing a cell containing an expression vector comprising a bbc3 gene promoter operably linked to either a polynucleotide encoding bbc3 or a polynucleotide encoding a heterologous reporter protein,
   b. exposing said cell to a candidate compound, and
   c. determining expression of said polynucleotide encoding Bbc3 or said polynucleotide encoding a heterologous reporter protein,
   wherein a change in expression is an indication that said candidate compound modulates apoptosis, and wherein said bbc3 gene promoter is a polynucleotide selected from the group consisting of (a) a polynucleotide comprising nucleotides 1–2099 of SEQ ID NO: 1, (b) a polynucleotide comprising nucleotides 1168–2099 of SEQ ID NO: 1, (c) a polynucleotide comprising nucleotides 1934–2099 of SEQ ID NO: 1, (d) a polynucleotide comprising a polynucleotide sequence having at least about 95% homology to bases 1–2099 of SEQ ID NO: 1, (e) a polynucleotide comprising a polynucleotide sequence having at least about 95% homology to bases 1168–2099 of SEQ ID NO:1, and (f) a polynucleotide comprising a polynucleotide sequence having at least about 95% homology to bases 1934–2099 of SEQ ID NO:1, wherein each of said nolynucleotides (a)–(f) has promoter activity for said polynucleotide encoding a heterologous reporter protein.

2. The method according to claim 1, wherein said determining expression is performed by detecting expression of bbc3 mRNA or heterologous reporter protein mRNA.

3. The method according to claim 1, wherein said determining expression is performed by detecting expression of bbc3 or heterologous reporter protein.

4. The method according to claim 1, wherein said determining expression is performed by assaying the capacity of Bbc3 for inducing death of said cell.

5. The method according to claim 1, wherein said polynucleotide encoding a heterologous reporter protein is selected from the group consisting of a polynucleotide encoding a luciferase enzyme, an alkaline phosphatase enzyme, a β-galactosidase enzyme and a chloramphenicol acetyltransferase enzyme.

6. The method according to claim 1, further comprising exposing said cell to one or more inducers and/or inhibitors of apoptosis at any time before exposing said cell to said candidate compound.

7. The method according to claim 1, further comprising exposing said cell to one or more inducers and/or inhibitors of apoptosis at any time after exposing said cell to said candidate compound.

8. The method according to claim 1, further comprising exposing said cell to one or more inducers and/or inhibitors of apoptosis simultaneously with exposure of said cell to said candidate compound.

9. The method according to claim 6, 7 or 8, wherein said one or more inducers and/or inhibitors is selected from the group consisting of a growth factor, absence of a growth factor, an agent of DNA damage, a glucocorticoid, p53 and a kinase inhibitor.

10. A method for identifying a compound that modulates apoptosis, said method comprising:
    a. providing a cell containing an expression vector comprising a bbc3 gene promoter operably linked to either a polynucleotide encoding Bbc3 or a polynucleotide encoding a heterologous reporter protein,
    b. culturing said cell in the presence of serum,
    c. culturing said cell in the absence of serum,
    d. exposing said cell to a candidate compound, and
    e. determining expression expression of said polynucleotide encoding Bbc3 or said polynucleotide encoding a heterologous reporter protein,
    wherein a change in expression is an indication that said candidate compound modulates apoptosis, and wherein said bbc3 gene promoter is a polynucleotide selected from the group consisting of (a) a polynucleotide comprising nucleotides 1–2099 of SEQ ID NO: 1, (b) a polynucleotide comprising nucleotides 1168–2099 of SEQ ID NO: 1, (c) a polynucleotide comprising nucleotides 1934–2099 of SEQ ID NO: 1, (d) a polynucleotide comprising a polynucleotide sequence having at least about 95% homology to bases 1–2099 of SEQ ID NO: 1, (e) a polynucleotide comprising a polynucleotide sequence having at least about 95% homology to bases 1168–2099 of SEQ ID NO:1, and (f) a polynucleotide comprising a polynucleotide sequence having at least about 95% homology to bases 1934–2099 of SEQ ID NO:1, wherein each of said nolynucleotides (a)–(f) has promoter activity for said polynucleotide encoding a heterologous reporter protein.

11. The method according to claims 10, wherein the expression of said polynucleotide encoding Bbc3 or said polynucleotide encoding a heterologous reporter protein is down-regulated by said candidate compound.

12. The method according to claim 10, wherein the determining expression is performed by detecting expression of bbc3 mRNA or heterologous reporter protein mRNA.

13. The method according to claim 10, wherein the determining expression is performed by detecting expression of Bbc3 or heterologous reporter protein.

14. The method according to claim 10, wherein the determining expression is performed by assaying the capacity of Bbc3 for inducing death of said cell.

15. The method according to claim 10, wherein said polynucleotide encoding a heterologous reporter protein is selected from the group consisting of a polynucleotide encoding a luciferase enzyme, an alkaline phosphatase enzyme, a β-galactosidase enzyme and a chloramphenicol acetyltransferase enzyme.

16. The method according to claim 10, further comprising exposing said cell to one or more inducers and/or inhibitors of apoptosis at any time before exposing said cell to said candidate compound.

17. The method according to claim 10, further comprising exposing said cell to one or more inducers and/or inhibitors of apoptosis at any time after exposing said cell to said candidate compound.

18. The method according to claim 10, further comprising exposing said cell to one or more inducers and/or inhibitors of apoptosis simultaneously with exposure of said cell to said candidate compound.

19. The method according to claim 16, 17, or 18, wherein said one or more inducers and/or inhibitors is selected from the group consisting of a growth factor, absence of a growth factor, an agent of DNA damage, a glucocorticoid, p53 and a kinase inhibitor.

20. A method for identifying a compound that modulates apoptosis, said method comprising:
   a. providing a cell containing an expression vector comprising a bbc3 gene promoter operably linked to either a polynucleotide encoding Bbc3 or a polynucleotide encoding a heterologous reporter protein,
   b. culturing said cell in the presence of serum,
   c. culturing said cell in the absence of serum,
   d. exposing said cell to a compound known to inhibit bbc3 gene promoter activity,
   e. exposing said cell to a candidate compound, and
   f. determining expression of said polynucleotide encoding Bbc3 or said polynucleotide encoding a heterologous reporter protein,
   wherein a change in expression is an indication that said candidate compound modulates apoptosis, and wherein said bbc3 gene promoter is a polynucleotide having promoter activity selected from the group consisting of (a) a polynucleotide comprising nucleotides 1–2099 of SEQ ID NO: 1, (b) a polynucleotide comprising nucleotides 1168–2099 of SEQ ID NO: 1, (c) a polynucleotide comprising nucleotides 1934–2099 of SEQ ID NO: 1, (d) a polynucleotide comprising a polynucleotide sequence having at least about 95% homology to bases 1–2099 of SEQ ID NO:1 , (e) a polynucleotide comprising a polynucleotide sequence having at least about 95% homology to bases 1168–2099 of SEQ ID NO:1 , and (f) a polynucleotide comprising a polynucleotide sequence having at least about 95% homology to bases 1934–2099 of SEQ ID NO:1, wherein each of said polynucleotides (a)–(f) has promoter activity for said polynucleotide encoding a heterologous reporter protein.

21. The method according to claims 20, wherein the expression of said polynucleotide encoding Bbc3 or said polynucleotide encoding a heterologous reporter protein is up-regulated by said candidate compound.

22. The method according to claim 20, wherein the determining expression is performed by detecting expression of bbc3 mRNA or heterologous reporter protein mRNA.

23. The method according to claim 20, wherein the determining expression is performed by detecting expression of Bbc3 or heterologous reporter protein.

24. The method according to claim 20, wherein the determining expression is performed by assaying the capacity of Bbc3 for inducing death of said cell.

25. The method according to claim 20, wherein said polynucleotide encoding a heterologous reporter protein is selected from the group consisting of a polynucleotide encoding a luciferase enzyme, an alkaline phosphatase enzyme, a β-galactosidase enzyme and a chloramphenicol acetyltransferase enzyme.

26. The method according to claim 20, further comprising exposing said cell to one or more inducers and/or inhibitors of apoptosis at any time before exposing said cell to said candidate compound.

27. The method according to claim 20, further comprising exposing said cell to one or more inducers and/or inhibitors of apoptosis at any time after exposing said cell to said candidate compound.

28. The method according to claim 20, further comprising exposing said cell to one or more inducers and/or inhibitors of apoptosis simultaneously with exposure of said cell to said candidate compound.

29. The method according to claim 26, 27, or 28, wherein said one or more inducers and/or inhibitors is selected from the group consisting of a growth factor, absence of a growth factor, an agent of DNA damage, a glucocorticoid, p53 and a kinase inhibitor.

30. A method for identifying a compound that modulates bbc3 gene expression, said method comprising:
   a. providing a cell containing an expression vector comprising a bbc3 gene promoter operably linked to either a polynucleotide encoding Bbc3 or a polynucleotide encoding a heterologous reporter protein,
   b. exposing said cell to a candidate compound, and
   c. determining expression of said polynucleotide encoding Bbc3 or said polynucleotide encoding a heterologous reporter protein,
   wherein a change in expression is an indication that said candidate compound modulates bbc3 gene expression, and wherein said bbc3 gene promoter is a polynucleotide selected from the group consisting of (a) a polynucleotide comprising nucleotides 1–2099 of SEQ ID NO: 1, (b) a polynucleotide comprising nucleotides 1168–2099 of SEQ ID NO: 1, (c) a polynucleotide comprising nucleotides 1934–2099 of SEQ ID NO: 1, (d) a polynucleotide comprising a polynucleotide sequence having at least about 95% homology to bases 1–2099 of SEQ ID NO:1, (e) a polynucleotide comprising a polynucleotide sequence having at least about 95% homology to bases 1168–2099 of SEQ ID NO:1, and (f) a polynucleotide comprising a polynucleotide sequence having at least about 95% homology to bases 1934–2099 of SEQ ID NO:1, wherein each of said polynucleotides (a)–(f) has promoter activity for said polynucleotide encoding a heterologous reporter protein.

31. The method according to claim 30, wherein the determining expression is performed by detecting expression of bbc3 mRNA or heterologous reporter protein mRNA.

32. The method according to claim 30, wherein the determining expression is performed by detecting expression of Bbc3 or heterologous reporter protein.

33. The method according to claim 30, wherein the determining expression is performed by assaying the capacity of Bbc3 for inducing death of said cell.

34. The method according to claim 30, wherein said polynucleotide encoding a heterologous reporter protein is selected from the group consisting of a polynucleotide encoding a luciferase enzyme, an alkaline phosphatase enzyme, a β-galactosidase enzyme and a chloramphenicol acetyltransferase enzyme.

35. The method according to claim 30, further comprising exposing said cell to one or more inducers and/or inhibitors of bbc3 gene expression at any time before exposing said cell to said candidate compound.

36. The method according to claim 30, further comprising exposing said cell to one or more inducers and/or inhibitors of bbc3 gene expression at any time after exposing said cell to said candidate compound.

37. The method according to claim 30, further comprising exposing said cell to one or more inducers and/or inhibitors of bbc3 gene expression simultaneously with exposure of said cell to said candidate compound.

38. The method according to claim 35, 36, or 37, wherein said one or more inducers and/or inhibitors is selected from the group consisting of a growth factor, absence of a growth factor, an agent of DNA damage, a glucocorticoid, p53 and a kinase inhibitor.

39. A method for identifying a compound that modulates bbc3 gene expression, said method comprising:
  a. providing a cell containing an expression vector comprising a bbc3 gene promoter operably linked to either a polynucleotide encoding Bbc3 or a polynucleotide encoding a heterologous reporter protein,
  b. culturing said cell in the presence of serum,
  c. culturing said cell in the absence of serum,
  d. exposing said cell to a candidate compound, and
  e. determining expression of said polynucleotide encoding Bbc3 or said polynucleotide encoding a heterologous reporter protein,
  wherein a change in expression is an indication that said candidate compound modulates bbc3 gene expression, and wherein said bbc3 gene promoter is a polynucleotide selected from the group consisting of (a) a polynucleotide comprising nucleotides 1–2099 of SEQ ID NO: 1, (b) a polynucleotide comprising nucleotides 1168–2099 of SEQ ID NO: 1, (c) a polynucleotide comprising nucleotides 1934–2099 of SEQ ID NO: 1, (d) a polynucleotide comprising a polynucleotide sequence having at least about 95% homology to bases 1–2099 of SEQ ID NO:1, (e) a polynucleotide comprising a polynucleotide sequence having at least about 95% homology to bases 1168–2099 of SEQ ID NO:1, and (f) a polynucleotide comprising a polynucleotide sequence having at least about 95% homology to bases 1934–2099 of SEQ ID NO:1, wherein each of said polynucleotides (a)–(f) has promoter activity for said polynucleotide encoding a heterologous reporter protein.

40. The method according to claims 39, wherein the expression of said polynucleotide encoding Bbc3 or said polynucleotide encoding a heterologous reporter protein is down-regulated by said candidate compound.

41. The method according to claim 39, wherein the determining expression is performed by detecting expression of bbc3 mRNA or heterologous reporter protein mRNA.

42. The method according to claim 39, wherein the determining expression is performed by detecting expression of Bbc3 or heterologous reporter protein.

43. The method according to claim 39, wherein the determining expression is performed by assaying the capacity of Bbc3 for inducing death of said cell.

44. The method according to claim 39, wherein said polynucleotide encoding a heterologous reporter protein is selected from the group consisting of a polynucleotide encoding a luciferase enzyme, an alkaline phosphatase enzyme, a β-galactosidase enzyme and a chloramphenicol acetyltransferase enzyme.

45. The method according to claim 39, further comprising exposing said cell to one or more inducers and/or inhibitors of bbc3 gene expression at any time before exposing said cell to said candidate compound.

46. The method according to claim 39, further comprising exposing said cell to one or more inducers and/or inhibitors of bbc3 gene expression at any time after exposing said cell to said candidate compound.

47. The method according to claim 39, further comprising exposing said cell to one or more inducers and/or inhibitors of bbc3 gene expression simultaneously with exposure of said cell to said candidate compound.

48. The method according to claim 45, 46, or 47, wherein said one or more inducers and/or inhibitors is selected from the group consisting of a growth factor, absence of a growth factor, an agent of DNA damage, a glucocorticoid, p53 and a kinase inhibitor.

49. A method for identifying a compound that modulates bbc3 gene expression, said method comprising:
  a. providing a cell containing an expression vector comprising a bbc3 gene promoter operably linked to either a polynucleotide encoding Bbc3 or a polynucleotide encoding a heterologous reporter protein,
  b. culturing said cell in the presence of serum,
  c. culturing said cell in the absence of serum,
  d. exposing said cell to a compound known to inhibit bbc3 gene promoter activity,
  e. exposing said cell to a candidate compound, and
  f. determining expression of said polynucleotide encoding Bbc3 or said polynucleotide encoding a heterologous reporter protein,
  wherein a change in expression is an indication that said candidate compound modulates bbc3 gene expression, and wherein said bbc3 gene promoter is a polynucleotide selected from the group consisting of (a) a polynucleotide comprising nucleotides 1–2099 of SEQ ID NO: 1, (b) a polynucleotide comprising nucleotides 1168–2099 of SEQ ID NO: 1, (c) a polynucleotide comprising nucleotides 1934–2099 of SEQ ID NO: 1, (d) a polynucleotide comprising a polynucleotide sequence having at least about 95% homology to bases 1–2099 of SEQ ID NO:1, (e) a polynucleotide comprising a polynucleotide sequence having at least about 95% homology to bases 1168–2099 of SEQ ID NO:1, and (f) a polynucleotide comprising a polynucleotide sequence having at least about 95% homology to bases 1934–2099 of SEQ ID NO:1, wherein each of said polynucleotides (a)–(f) has promoter activity for said polynucleotide encoding a heterologous reporter protein.

50. The method according to claims 49, wherein the expression of said polynucleotide encoding Bbc3 or said polynucleotide encoding a heterologous reporter protein is up-regulated by said candidate compound.

51. The method according to claim 49, wherein the determining expression is performed by detecting expression of bbc3 mRNA or heterologous reporter protein mRNA.

52. The method according to claim 49, wherein the determining expression is performed by detecting expression of Bbc3 or heterologous reporter protein.

53. The method according to claim 49, wherein the determining expression is performed by assaying the capacity of Bbc3 for inducing death of said cell.

54. The method according to claim 49, wherein the polynucleotide encoding a heterologous reporter protein is selected from the group consisting of a polynucleotide encoding a luciferase enzyme, an alkaline phosphatase enzyme, a β-galactosidase enzyme and a chloramphenicol acetyltransferase enzyme.

55. The method according to claim 49, further comprising exposing said cell to one or more inducers and/or inhibitors of bbc3 gene expression at any time before exposing said cell to said candidate compound.

56. The method according to claim 49, further comprising exposing said cell to one or more inducers and/or inhibitors of bbc3 gene expression at any time after exposing said cell to said candidate compound.

57. The method according to claim 49, further comprising exposing said cell to one or more inducers and/or inhibitors of bbc3 gene expression simultaneously with exposure of said cell to said candidate compound.

58. The method according to claim 55, 56, or 57, wherein said one or more inducers and/or inhibitors is selected from the group consisting of a growth factor, absence of a growth factor, an agent of DNA damage, a glucocorticoid, p53 and a kinase inhibitor.

59. A method for identifying a compound that modulates gene expression, said method comprising:
  a. providing a polynucleotide construct having promoter activity operably linked to either a polynucleotide encoding Bbc3 or a polynucleotide encoding a heterologous reporter protein,
  b. exposing said polynucleotide construct to a candidate compound, and
  c. determining expression of said polynucleotide encoding Bbc3 or said polynucleotide encoding a heterologous reporter protein,
  wherein a change in expression is an indication that said candidate compound modulates gene expression, and wherein said polynucleotide is selected from the group consisting of (a) a polynucleotide comprising nucleotides 1–2099 of SEQ ID NO: 1, (b) a polynucleotide comprising nucleotides 1168–2099 of SEQ ID NO: 1, (c) a polynucleotide comprising nucleotides 1934–2099 of SEQ ID NO: 1, (d) a polynucleotide comprising a polynucleotide sequence having at least about 95% homology to bases 1–2099 of SEQ ID NO:1, (e) a polynucleotide comprising a polynucleotide sequence having at least about 95% homology to bases 1168–2099 of SEQ ID NO:1, and (f) a polynucleotide comprising a polynucleotide sequence having at least about 95% homology to bases 1934–2099 of SEQ ID NO:1, wherein each of said polynucleotides (a)–(f) has promoter activity for said polynucleotide encoding a heterologous reporter protein.

60. The method according to claim 59, wherein the determining expression is performed by detecting expression of bbc3 mRNA or heterologous reporter protein mRNA.

61. The method according to claim 59, wherein the determining expression is performed by detecting expression of Bbc3 or heterologous reporter protein.

62. The method according to claim 59, wherein said polynucleotide encoding a heterologous reporter protein is selected from the group consisting of a polynucleotide encoding a luciferase enzyme, an alkaline phosphatase enzyme, a β-galactosidase enzyme and a chloramphenicol acetyltransferase enzyme.

63. The method according to claim 59, further comprising exposing said composition to one or more inducers and/or inhibitors of bbc3 gene expression at any time before exposing said composition to said candidate compound.

64. The method according to claim 59, further comprising exposing said composition to one or more inducers and/or inhibitors of bbc3 gene expression at any time after exposing said composition to said candidate compound.

65. The method according to claim 59, further comprising exposing said composition to one or more inducers and/or inhibitors of bbc3 gene expression simultaneously with exposure of said composition to said candidate compound.

66. The method according to claim 63, 64, or 65, wherein said one or more inducers and/or inhibitors is selected from the group consisting of a growth factor, absence of a growth factor, an agent of DNA damage, a glucocorticoid, p53 and a kinase inhibitor.

67. A method for identifying a compound that interacts with a polynucleotide having promoter activity, said method comprising:
  a. providing a polynucleotide having promoter activity,
  b. contacting said polynucleotide with a candidate compound, and
  c. detecting an interaction between said polynucleotide and said candidate compound,
  thereby identifying a compound that interacts with a polynucleotide having promoter activity, wherein said polynucleotide is selected from the group consisting of (a) a polynucleotide comprising nucleotides 1–2099 of SEQ ID NO: 1, (b) a polynucleotide comprising nucleotides 1168–2099 of SEQ ID NO: 1, (c) a polynucleotide comprising nucleotides 1934–2099 of SEQ ID NO: 1, (d) a polynucleotide comprising a polynucleotide sequence having at least about 95% homology to bases 1–2099 of SEQ ID NO:1, (e) a polynucleotide comprising a polynucleotide sequence having at least about 95% homology to bases 1168–2099 of SEQ ID NO:1, and (f) a polynucleotide comprising a polynucleotide sequence having at least about 95% homology to bases 1934–2099 of SEQ ID NO:1, wherein each of said polynucleotides (a)–(f) has promoter activity for a polynucleotide encoding a heterologous reporter protein.

68. The method according to claim 67, wherein said detecting an interaction is performed using an antibody that recognizes and binds said candidate compound.

69. The method according to claim 67, wherein said detecting an interaction is performed using polymerase chain reaction.

70. The method according to claim 67, wherein said detecting an interaction is performed by gel retardation analysis.

71. The method according to claim 67, wherein said polynucleotide having promoter activity is in a cell and said cell is contacted with said candidate compound.

72. An isolated nucleic acid molecule comprising the polynucleotide sequence of bases 1–2099 of SEQ ID NO: 1, wherein said nucleic acid molecule has promoter activity for a polynucleotide encoding a heterologous reporter protein.

73. An isolated nucleic acid molecule comprising the polynucleotide sequence of bases 1168–2099 of SEQ ID NO: 1, wherein said nucleic acid molecule has promoter activity for a polynucleotide encoding a heterologous reporter protein.

74. An isolated nucleic acid molecule comprising the polynucleotide sequence of bases 1934–2099 of SEQ ID NO: 1, wherein said nucleic acid molecule has promoter activity for a polynucleotide encoding a heterologous reporter protein.

75. An isolated nucleic acid molecule comprising a polynucleotide sequence having at least about 95% homology to bases 1–2099 of SEQ ID NO: 1, wherein said nucleic acid molecule has promoter activity for a polynucleotide encoding a heterologous reporter protein.

76. An isolated nucleic acid molecule comprising a polynucleotide sequence having at least about 95% homology to bases 1168–2099 of SEQ ID NO: 1, wherein said nucleic acid molecule has promoter activity for a polynucleotide encoding a heterologous reporter protein.

77. An isolated nucleic acid molecule comprising a polynucleotide sequence having at least about 95% homology to bases 1934–2099 of SEQ ID NO: 1, wherein said nucleic acid molecule has promoter activity for a polynucleotide encoding a heterologous reporter protein.

78. An isolated nucleic acid molecule consisting of the polynucleotide sequence of bases 1–2099 of SEQ ID NO: 1.

79. An isolated nucleic acid molecule consisting of the polynucleotide sequence of bases 1168–2099 of SEQ ID NO: 1.

80. An isolated nucleic acid molecule consisting of the polynucleotide sequence of bases 1934–2099 of SEQ ID NO: 1.

81. An isolated nucleic acid molecule consisting of a polynucleotide sequence at least about 95% homologous to bases 1–2099 of SEQ ID NO: 1, wherein said nucleic acid molecule has promoter activity.

82. An isolated nucleic acid molecule consisting of a polynucleotide sequence at least about 95% homologous to bases 1168–2099 of SEQ ID NO: 1, wherein said nucleic acid molecule has promoter activity.

83. An isolated nucleic acid molecule consisting of a polynucleotide sequence at least about 95% homologous to bases 1934–2099 of SEQ ID NO: 1, wherein said nucleic acid molecule has promoter activity.

* * * * *

SEQUENCE LISTING

<160> NUMBER OF SEQ ID NOS: 1

<210> SEQ ID NO 1
<211> LENGTH: 2104
<212> TYPE: DNA
<213> ORGANISM: Homo sapiens

<400> SEQUENCE: 1

```
ggatcccgag gtcaggagtt tgagaccagc ctggccaata tggtgaaacc gcatctctac      60
caataataca aaaattagct gggcatagtg gcgcacacct gtagtcccag ctactaggga     120
ggctgaggca aagacttgc ttgaacccag gaggcggagg tggcaatgag ccgagatcat     180
gccactgaac tccagcctgg cgacagcgc gagactctgt ctcaaaaaaa aaaaaaaaag     240
taagatccat gtaagtgatg tcatatgtca taatccatgg tttactcatg acccacagtt     300
tggaaaacac caggaagaag gaagggacaa tgaataatcg gggaaagcga agaggaggg     360
aaagtgaaag agggaggaaa gctgaggagt tcccaatgtt gcaaatgggg agatttcacg     420
tgagatatag attacctgca tctcttgggg gagctaagag tgtgtacttg gaggcagtca     480
agtttgagaa gtctgacatc cttactcagc cagccccaca ctaggcactg aaggtgagt     540
cactctggtg aggcgattgc gattgggtga acccagtaa ggatgaaaag tgtagaggag     600
acaggaatcc acggctttgg aaaaaggaag gacaaaactc accaaaccag agcagggcag     660
gaagtaacaa tgagaaactg aaaaagaaac ggaatggaaa gctatgagac aggatgaaat     720
ttggcatggg gtctgcccag gcatgtccat gccaggtgcc cagggctgct ccacgacgt     780
gggtcccctg ccagatttgt ggtgagtgt gccaggtgtg catgctccga cgtgtgtgca     840
gtgggccagt tagcaagaag ctgtcacagg tgtgactttg tgacatgtgt gggtggtcag     900
tttcttctat gtctgatttg gtttgtgtct ctgaatgtca gtttctttcc tttatttta     960
tttttaagac ggagtttgct cttgttgccc aggctagagt gcaatggcac tatctcggct    1020
cactgcaacc tccgcctccc gggttcaagc agttctcctg cctcagcctc ccaagtagct    1080
gggattacag gcatgcgcca caacgcccgg ctaattttgt attttagta gagatggggt    1140
ttcatcatgt tggtcaggct ggtctcgaat tcctgacctc aggcagtcca cgcaccttgg    1200
cctcccaaag tgctgggatt acaggcatga gccaccgtgt cgggcgaatg tcactttctg    1260
atagttttaa tgtgttagct gtgaaattgt gtgagtgcat ttgtgtatgt ccctgtggga    1320
gtgtgatttg gatttggccg tgtatccagg tatccctgta acaggtgtct gtgtgtatgt    1380
gtgtgtcccc tgtgcctatc agcaagtttg tgtttcctga taagcactcc gcctatgtct    1440
gtgtggttgc accaccgtgt gtgtggtgtg ggtgcctgtt cggtagggtt gtttgtgaac    1500
acagtttgtg ggcccaggtg tgatcatcag tgtgggtgtt tctgcaactg tgtgtggccc    1560
tgtcattgtg tccgtctgct tgtccagggg accctgttag tgagtctgtg catttccgtc    1620
tgggtgtgtg taagtgtgag ccccatcagt atgtgagtgt gtgtgctcat gccctgtcc    1680
atggtgtgga tttgcgagac tgtggccttg tgtctgtgag tacatcctct gggctctgcc    1740
tgcacgtgac tttgtggacc ctgaacgcc cgtcggtcgg tctgtgtacg catcgctggg    1800
ggtgtggatc tgtgggtccc agtcagtgtg tgtgtccgac tgtcccggtg tctgggcgat    1860
ctccccacac cccgccgcac agcgcctggg tcctccttgc cttgggctag ccctgcccc    1920
gtccccccgct gcagggaaac cccggcgcg gaggtagggg gggcgcggc gcgcgcctgc    1980
aagtcctgac ttgtccgcgg cgggcgggcg gggccgtagc gtcacgcggg ggcggggcgt    2040
```

-continued

```
gggacccgcc gggcgggggc ggggcggggc ggggcggggc ggctttggag cgggcccggg    2100
atcc                                                                 2104
```